US010679384B2

(12) United States Patent
Palma et al.

(10) Patent No.: US 10,679,384 B2
(45) Date of Patent: Jun. 9, 2020

(54) SYSTEMS AND METHODS FOR DEEP LEARNING-BASED IMAGE RECONSTRUCTION

(71) Applicant: General Electric Company, Schenectady, NY (US)

(72) Inventors: Giovanni John Jacques Palma, Buc (FR); Razvan Iordache, Buc (FR)

(73) Assignee: General Electric Company, Schenectady, NY (US)

( * ) Notice: Subject to any disclaimer, the term of this patent is extended or adjusted under 35 U.S.C. 154(b) by 7 days.

(21) Appl. No.: 15/720,632

(22) Filed: Sep. 29, 2017

(65) Prior Publication Data

US 2019/0102916 A1    Apr. 4, 2019

(51) Int. Cl.
| G06K 9/00 | (2006.01) |
| G06T 11/00 | (2006.01) |
| A61B 6/00 | (2006.01) |
| A61B 6/02 | (2006.01) |
| G06N 3/04 | (2006.01) |
| G06N 3/08 | (2006.01) |
| G06T 7/33 | (2017.01) |

(52) U.S. Cl.
CPC ............ *G06T 11/005* (2013.01); *A61B 6/025* (2013.01); *A61B 6/5205* (2013.01); *A61B 6/5258* (2013.01); *G06N 3/04* (2013.01); *G06N 3/08* (2013.01); *G06T 7/33* (2017.01); *G06T 11/006* (2013.01); *G06T 2211/436* (2013.01)

(58) Field of Classification Search
CPC ................. G06F 19/321; G06T 7/0012; G06T 2207/10081; G06T 2210/41; G06T 2207/10072; G06K 9/66; G06K 9/52
See application file for complete search history.

(56) References Cited

U.S. PATENT DOCUMENTS

| 8,452,379 B2 | 5/2013 | DeFreitas et al. |
| 9,449,403 B2* | 9/2016 | Jerebko .................. A61B 6/025 |
| 10,096,106 B2 | 10/2018 | Bernard |
| 2003/0006770 A1* | 1/2003 | Smith ..................... F23C 6/045 |
| | | 324/309 |

(Continued)

OTHER PUBLICATIONS

European Patent Office, "European Search Report," issued in connection with European Patent Application No. 18193060.3, dated Feb. 13, 2019, 8 pages.

(Continued)

*Primary Examiner* — Guillermo M Rivera-Martinez
(74) *Attorney, Agent, or Firm* — Hanley, Flight & Zimmerman, LLC

(57) ABSTRACT

Methods and systems for deep learning based image reconstruction are disclosed herein. An example method includes receiving a set of imaging projections data, identifying a voxel to reconstruct, receiving a trained regression model, and reconstructing the voxel. The voxel is reconstructed by: projecting the voxel on each imaging projection in the set of imaging projections according to an acquisition geometry, extracting adjacent pixels around each projected voxel, feeding the regression model with the extracted adjacent pixel data to produce a reconstructed value of the voxel, and repeating the reconstruction for each voxel to be reconstructed to produce a reconstructed image.

19 Claims, 22 Drawing Sheets

(56) References Cited

U.S. PATENT DOCUMENTS

| | | | |
|---|---|---|---|
| 2005/0135664 A1* | 6/2005 | Kaufhold | G06T 11/006 382/131 |
| 2005/0220265 A1* | 10/2005 | Besson | A61B 6/032 378/16 |
| 2005/0285042 A1* | 12/2005 | Joung | G01T 1/1644 250/363.02 |
| 2008/0050002 A1* | 2/2008 | Arnold | A61B 5/02007 382/131 |
| 2011/0092793 A1* | 4/2011 | Thomson | A61B 6/032 600/407 |
| 2011/0142316 A1* | 6/2011 | Wang | G06T 11/006 382/131 |
| 2011/0311129 A1* | 12/2011 | Milanfar | G06K 9/00335 382/154 |
| 2014/0072108 A1* | 3/2014 | Rohler | A61B 6/482 378/207 |
| 2014/0185896 A1* | 7/2014 | Baturin | A61B 6/032 382/131 |
| 2014/0294138 A1* | 10/2014 | Jerebko | A61B 6/025 378/4 |
| 2015/0092916 A1* | 4/2015 | Baturin | G01N 23/20075 378/36 |
| 2015/0196265 A1* | 7/2015 | Suzuki | G06K 9/6262 378/37 |
| 2015/0213633 A1* | 7/2015 | Chang | G01N 23/046 382/284 |
| 2015/0347682 A1* | 12/2015 | Chen | G16H 50/30 705/2 |
| 2016/0183901 A1 | 6/2016 | Bernard | |
| 2016/0310019 A1* | 10/2016 | Fonte | A61B 6/504 |
| 2017/0071562 A1* | 3/2017 | Suzuki | A61B 6/5205 |
| 2017/0160211 A1* | 6/2017 | Schulte | A61B 6/14 |
| 2017/0248708 A1* | 8/2017 | Bordy | A61N 5/1071 |
| 2018/0140265 A1* | 5/2018 | Chu | A61N 5/1049 |

OTHER PUBLICATIONS

Abdurahman, et al., "Out-of-Plane Artifact Reduction in Tomosynthesis Based on Regression Modeling and Outlier Detection," Springer-Verlag Berlin Heidelberg, Jul. 8, 2012, pp. 729-736.

Hammernik K, et al., "A deep learning architecture for limited-angle computed tomography reconstruction," Bildverarbeitung Fur Die Medizin 2017: Algorithmen-Systeme-Anwendungen: Proceedings Des Workshops VOM 12., Bis 14., Mar. 12, 2017, pp. 92-97.

* cited by examiner

… (1) …

SYSTEMS AND METHODS FOR DEEP LEARNING-BASED IMAGE RECONSTRUCTION

FIELD OF THE DISCLOSURE

This disclosure relates generally to image reconstruction, and, more particularly, to systems and methods for deep learning-based image reconstruction.

BACKGROUND

In recent years, digital breast tomosynthesis (DBT) and contrast-enhanced digital breast tomosynthesis (CE-DBT) have proved to be effective cancer detection techniques. DBT creates a three-dimensional (3D) image of the breast using x-rays. By taking multiple x-ray pictures of each breast from many angles, a computer can generate a 3D image used to detect any abnormalities. A critical part of the DBT/CE-DBT process is image reconstruction as it directly impacts the content of the data that the radiologists will review to determine any diagnosis. To reconstruct the image, algorithms trained and used to reduce the noise and any streak lines. Despite the complexity of the algorithms, the DBT process typically results in non-perfect image reconstruction.

Figure 1A:
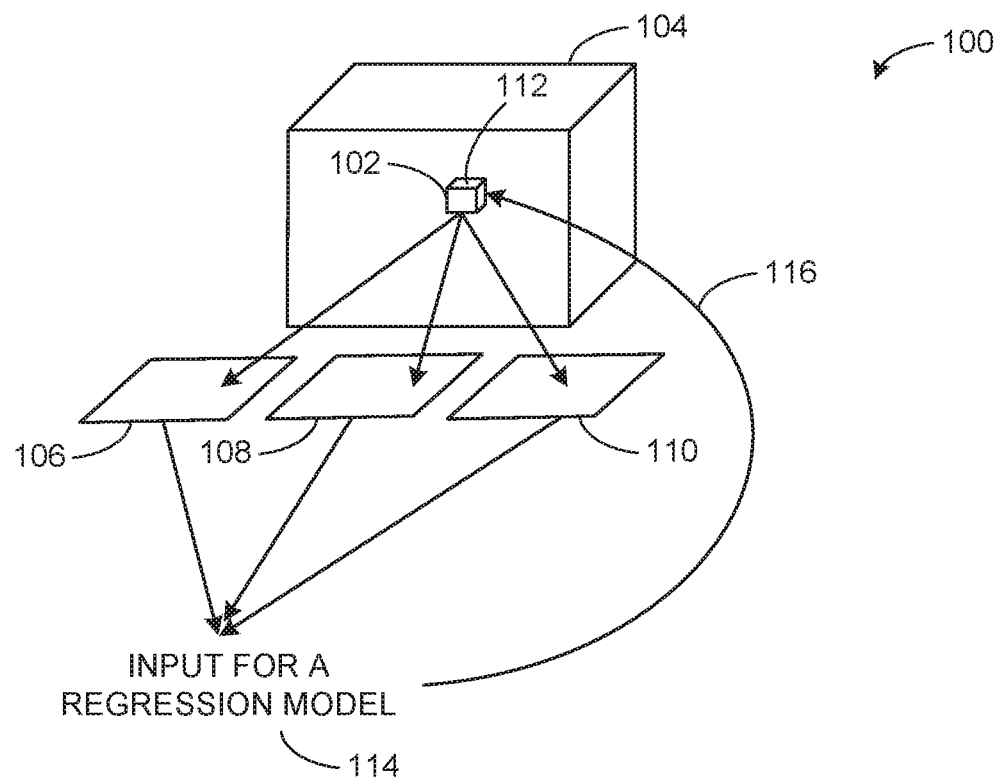
FIG. 1A illustrates an example diagram representing the reconstruction of a voxel using imaging projection data.

The figures are not to scale. Instead, to clarify multiple layers and regions, the thickness of the layers may be enlarged in the drawings. Wherever possible, the same reference numbers will be used throughout the drawing(s) and accompanying written description to refer to the same or like parts. As used in this patent, stating that any part (e.g., a layer, film, area, or plate) is in any way positioned on (e.g., positioned on, located on, disposed on, or formed on, etc.) another part, means that the referenced part is either in contact with the other part, or that the referenced part is above the other part with one or more intermediate part(s) located there between. Stating that any part is in contact with another part means that there is no intermediate part between the two parts.

BRIEF SUMMARY

Certain examples provide methods and systems for deep learning based image reconstruction.

An example method disclosed herein includes receiving a set of imaging projection data, identifying a voxel to reconstruct, and receiving a trained regression model. The example method further includes reconstructing the voxel by: projecting the voxel onto each imaging projection in the set of projections according to an acquisition geometry, extracting adjacent pixels around each projected voxel, feeding the regression model with the extracted adjacent pixel data to produce a reconstructed value of the reconstructed model, and repeating the reconstruction for each voxel to be reconstructed to produce a reconstructed image.

An example system disclosed herein includes a regression model trainer to train a regression model, a voxel identifier to identify a voxel to be reconstructed, an imaging projections data receiver to receive a set of imaging projections, and a voxel reconstructor. The voxel reconstructor includes a voxel projector to project the voxel onto each imaging projection in the set of imaging projections according to an acquisition geometry, an adjacent pixel extractor to extract adjacent pixels around each projected voxel, and a regression model feeder to feed the regression model with the extracted adjacent pixel data to produce a reconstructed value of the voxel.

An example non-transitory computer readable storage medium disclosed herein includes instructions which, when executed, cause a machine to at least receive a set of projections data, identify a voxel to reconstruct, receive a trained regression model, and reconstruct the voxel by: projecting the voxel onto each imaging projection in the set of imaging projections according to an acquisition geometry, extracting adjacent pixels around each projected voxel, feeding the regression model with the extracted adjacent pixel data to produce a reconstructed value of the voxel, and repeating the reconstruction for each voxel to be reconstructed to produce a reconstructed image.

An example method disclosed herein includes receiving a set of imaging projection data, identifying a pixel to reconstruct, receiving a trained regression model, and reconstructing the pixel. Reconstructing the pixel includes mapping the pixel onto each imaging projection in the set of projections according to an acquisition geometry, extracting adjacent pixels around each mapped pixel, feeding the regression model with the extracted adjacent pixel data to produce a reconstructed value of the pixel, and repeating the reconstruction for each pixel to be reconstructed.

An example system disclosed herein includes a regression model trainer to train a regression model, a pixel identifier to identify a pixel to be reconstructed, an imaging projections data receiver to receive a set of imaging projections, and a pixel reconstructor. The pixel reconstructor includes a pixel mapper to map the pixel on each imaging projection in the set of imaging projections according to an acquisition geometry, an adjacent pixel extractor to extract adjacent pixels around each mapped pixel, and a regression model feeder to feed the regression model with the extracted adjacent pixel data to produce a reconstructed value for the pixel.

An example non-transitory computer readable storage medium comprising instructions which, when executed, cause a machine to at least receive a set of imaging projection data, identify a pixel to reconstruct, receive a trained regression model, and reconstruct the pixel. Reconstructing the pixel includes mapping the pixel on each imaging projection in the set of imaging projections according to an acquisition geometry, extracting adjacent pixels around each mapped pixel, feeding the regression model with the extracted adjacent pixel data to produce a reconstructed value of the pixel, and repeating the reconstruction for each pixel to be reconstructed.

An example method disclosed herein includes receiving a volume, identifying a pixel to reconstruct, receiving a trained regression model, and reconstructing the pixel. Reconstructing the pixel includes mapping the pixel onto voxels from the volume according to an acquisition geometry, extracting adjacent voxels around each mapped pixel, feeding the regression model with the extracted adjacent voxel data to produce a reconstructed value of the pixel, and repeating the reconstruction for each pixel to be reconstructed.

An example system disclosed herein includes a regression model trainer to train a regression model, a pixel identifier to identify a pixel to be reconstructed, a volume receiver to receive a volume, and a pixel reconstructor. The pixel reconstructor includes a pixel mapper to map the pixel onto voxels from the volume according to an acquisition geometry, an adjacent voxel extractor to extract adjacent voxels around each mapped pixel, and a regression model feeder to feed the regression model with the extracted adjacent voxel data to produce a reconstructed value for the pixel.

An example non-transitory computer readable storage medium comprising instructions which, when executed, cause a machine to at least receive a volume, identify a pixel to reconstruct, receive a trained regression model, and reconstruct the pixel. Reconstructing the pixel includes mapping the pixel onto voxels from the volume according to an acquisition geometry, extracting adjacent voxels around each mapped pixel, feeding the regression model with the extracted adjacent voxel data to produce a reconstructed value of the pixel, and repeating the reconstruction for each pixel to be reconstructed.

An example method disclosed herein includes receiving a set of imaging projection data, receiving a volume, identifying a pixel to reconstruct, receiving a trained regression model, and reconstructing the pixel. Reconstructing the pixel includes mapping the pixel onto each imaging projection in the set of projections according to an acquisition geometry, mapping the pixel onto voxels from the volume according to an acquisition geometry, extracting adjacent pixels around each mapped pixel in the projections, extracting adjacent voxels around each mapped pixel in the volume, feeding the regression model with the extracted adjacent pixel data and extracted adjacent voxel data to produce a reconstructed value of the pixel, and repeating the reconstruction for each pixel to be reconstructed.

An example system disclosed herein includes a regression model trainer to train a regression model, a pixel identifier to identify a pixel to be reconstructed, an imaging projections data receiver to receive a set of imaging projections, a volume receiver to receive a volume and a pixel reconstructor. The pixel reconstructor includes a pixel mapper to map the pixel on each imaging projection in the set of imaging projections according to an acquisition geometry and to map the pixel onto voxels from the volume according to an acquisition geometry, an adjacent pixel extractor to extract adjacent pixels around each mapped pixel in the imaging projections, an adjacent voxel extractor to extract adjacent voxels around the mapped pixel in the volume, and a regression model feeder to feed the regression model with the extracted adjacent pixel data and the extracted adjacent voxel data to produce a reconstructed value for the pixel.

An example non-transitory computer readable storage medium comprising instructions which, when executed, cause a machine to at least receive a set of imaging projection data, receive a volume, identify a pixel to reconstruct, receive a trained regression model, and reconstruct the pixel. Reconstructing the pixel includes mapping the pixel on each imaging projection in the set of imaging projections according to an acquisition geometry, mapping the pixel onto voxels from the volume according to an acquisition geometry, extracting adjacent pixels around each mapped pixel in the projections, extracting adjacent voxels around the mapped pixel in the volume, feeding the regression model with the extracted adjacent pixel data to produce a reconstructed value of the pixel, and repeating the reconstruction for each pixel to be reconstructed.

An example method disclosed herein includes receiving a volume, receiving an orientation parameter and a thickness parameter for a slab to reconstruct, identifying a voxel from the slab to reconstruct, receiving a trained regression model, and reconstructing the voxel. Reconstructing the voxel includes mapping the voxel from the slab voxels from the volume according to the orientation parameter and the thickness parameter of the slab, extracting adjacent voxels from the volume around each mapped voxel from the slab, feeding the regression model with the extracted adjacent voxel from the volume data to produce a reconstructed value of the voxel from the slab, and repeating the reconstruction for each voxel from the slab to be reconstructed.

An example system disclosed herein includes a regression model trainer to train a regression model, a volume receiver to receive a volume, an orientation parameter receiver to receive an orientation parameter for a slab to reconstruct, a thickness parameter receiver to receive a thickness parameter for a slab to reconstruct, a voxel identifier to identify a voxel from the slab to be reconstructed, and a voxel reconstructor. The voxel reconstructor includes a voxel mapper to map the voxel from the slab onto voxels from the volume according to the orientation parameter and the thickness parameter of the slab, an adjacent voxel extractor to extract adjacent voxels from the volume around each mapped voxel from the slab, and a regression model feeder to feed the regression model with the extracted adjacent voxel from the volume data to produce a reconstructed value of the voxel from the slab.

An example non-transitory computer readable storage medium comprising instructions which, when executed, cause a machine to at least receive a volume, receive an orientation parameter and a thickness parameter for a slab to reconstruct, identify a voxel from the slab to reconstruct, receive a trained regression model, and reconstruct the voxel. Reconstructing the voxel includes mapping the voxel from the slab onto voxels from the volume according to the orientation parameter and the thickness parameter of the slab, extracting adjacent voxels from the volume around each mapped voxel from the slab, feeding the regression model with the extracted adjacent voxel from the volume data to produce a reconstructed value of the voxel from the slab, and repeating the reconstruction for each voxel from the slab to be reconstructed.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized. The following detailed description is therefore, provided to describe an exemplary implementation and not to be taken limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

As used herein, the terms "system," "unit," "module," etc., may include a hardware and/or software system that operates to perform one or more functions. For example, a module, unit, or system may include a computer processor, controller, and/or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules, units, engines, and/or systems shown in the attached figures may represent the hardware that operates based on software or hard-wired instructions, the software that directs hardware to perform the operations, or a combination thereof.

As used herein, the term "mapping" indicates translating a position of a location in an object being imaged to a corresponding location in one or more images obtained of the object. Alternatively or in addition, mapping can refer to a correlation between common points in a plurality of images or views such that a point in a first image is mapped to the same point in other related images such that their location coordinates are correlated when forming a synthetic two-dimensional image, three-dimensional volume, etc. For example, each element (e.g. a pixel, a voxel, etc.) in a 3D object has a location on a coordinate system. Mapping the elements in the 3D object indicates translating a data point from the 3D object to a corresponding data point in a generated 2D or 3D image.

As used herein, the term "projection" or "projection image" indicates an image obtained from emission of x-rays from a particular angle or view. A projection can be thought of as a particular example of mapping in which a set of projection images are captured from different angles of a 3D object and mapped or combined/fused to reconstruct a volume and/or create a synthetic 2D image. Each projection image is captured relative to a central projection (e.g. base projection, straight-on projection, zero angle projection, etc.). The resulting image from the projections is either a 3D reconstructed image that is approximately identical to the original 3D object or a synthetic 2D image that merges each projection together and benefits from the information in each view.

As used herein, the term "acquisition geometry" is a particular path or movement of an x-ray source with respect to a 3D object (e.g., detector) to obtain a series of 2D projections.

While certain examples are described below in the context of medical or healthcare workplaces, other examples can be implemented outside the medical environment.

In many different applications, deep learning techniques have utilized learning methods that allow a machine to be given raw data and determine the representations needed for data classification. Deep learning ascertains structure in data sets using back propagation algorithms which are used to alter internal parameters (e.g., node weights) of the deep learning machine. Deep learning machines can utilize a variety of multilayer architectures and algorithms. While machine learning, for example, involves an identification of features to be used in training the network, deep learning processes raw data to identify features of interest without the external identification.

Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters. Learning refines the machine parameters, and, by extension, the connections between neurons in the network, such that the neural network behaves in a desired manner.

Deep learning operates on the understanding that many datasets include high level features which include low level features. While examining an image, for example, rather than looking for an object, it is more efficient to look for edges which form motifs which form parts, which form the object being sought. These hierarchies of features can be found in many different forms of data such as speech and text, etc.

An example use of deep learning techniques in the medical field is mammography. Mammography is used to screen for breast cancer and other abnormalities. Traditionally, mammograms have been formed on x-ray film. However, more recently, flat panel digital imagers have been introduced that acquire a mammogram in digital form, and thereby facilitate analysis and storage of the acquired images. Further, substantial attention and technological development have been dedicated toward obtaining three-dimensional images of the breast. Three-dimensional (3D) mammography is also referred to as digital breast tomosynthesis (DBT). Two-dimensional (2D) mammography is full-field digital mammography, and synthetic 2D mammography produces 2D pictures derived from 3D data by combining individual enhanced slices (e.g., 1 mm, 2 mm, etc.) of a DBT volume. Breast tomosynthesis systems construct a 3D image volume from a series of two-dimensional (2D) projection images, each projection image obtained at a different angular displacement of an x-ray source. The constructed 3D image volume is typically presented as a plurality of slices of image data, the slices being geometrically reconstructed on planes parallel to the imaging detector.

Example Systems and Associated Methods

FIG. 1A illustrates an example diagram 100 representing the reconstruction of a voxel 102 using imaging projection data. The voxel 102 within a 3D space 104 is to be reconstructed. The voxel 102 is projected into a first 2D projected view 106, a second 2D projected view 108, and a third 2D projected view 110, each 2D projection representing a slice 112 of the voxel 102. Each 2D projected view 106, 108, 110 has a unique image value and position indicator. For example, the first 2D projected view 106 may have a unique image value of six and represent the top of the voxel 102. In the same example, the second 2D projected view 108 may have a unique image value of nine and represent the bottom of the voxel 102. Still further in the same example, the third 2D projected view 110 may have a unique image value of five and represent a side of the voxel 102. In this example, there are three 2D projected views. However, in other examples, there may be any number of 2D projected views, each 2D projected view representing an image slice 112 of the volume. The 2D projected views 106, 108, 110 provide an input for a regression model 114. This input for a regression model 114 is used to reconstruct 116 the voxel 102 to an approximately identical voxel. The process that the diagram 100 describes repeats until each voxel 102 within the 3D space 104 has been reconstructed. In this example, a voxel is being reconstructed. However, in other examples, any graphical element may be reconstructed (e.g., a pixel, a slab, etc.).

Figure 1B:
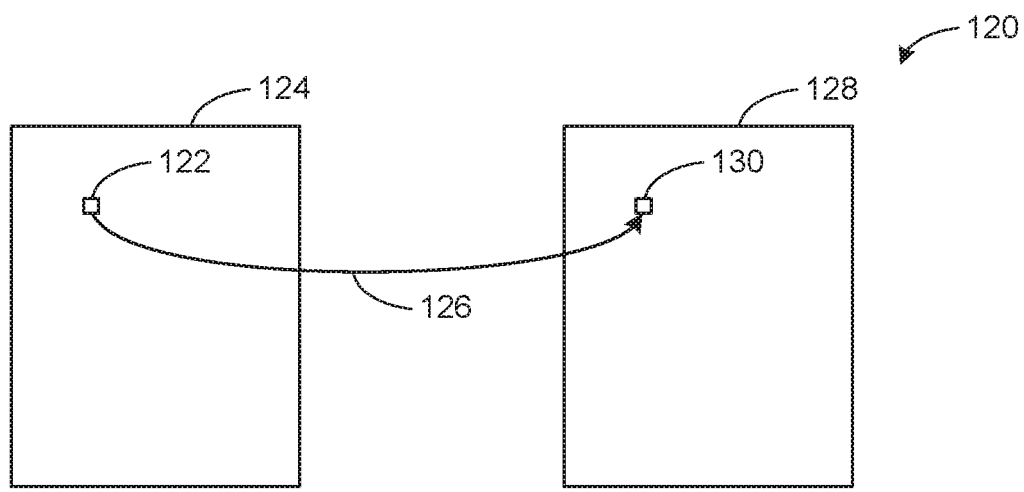
FIG. 1B illustrates an example diagram representing the reconstruction of a pixel using imaging projection data.

FIG. 1B illustrates an example diagram 120 representing the reconstruction of a pixel 122 within an image 124 using imaging projection data. While the voxel 102 of FIG. 1A is projected onto imaging projections, in this example, the pixel 122 is mapped 126 onto each imaging projection 128 in the set of projections according to an acquisition geometry. The mapping 126 of the pixel 122 results in an approximately identical pixel 130 on the imaging projection 128.

Figure 1C:
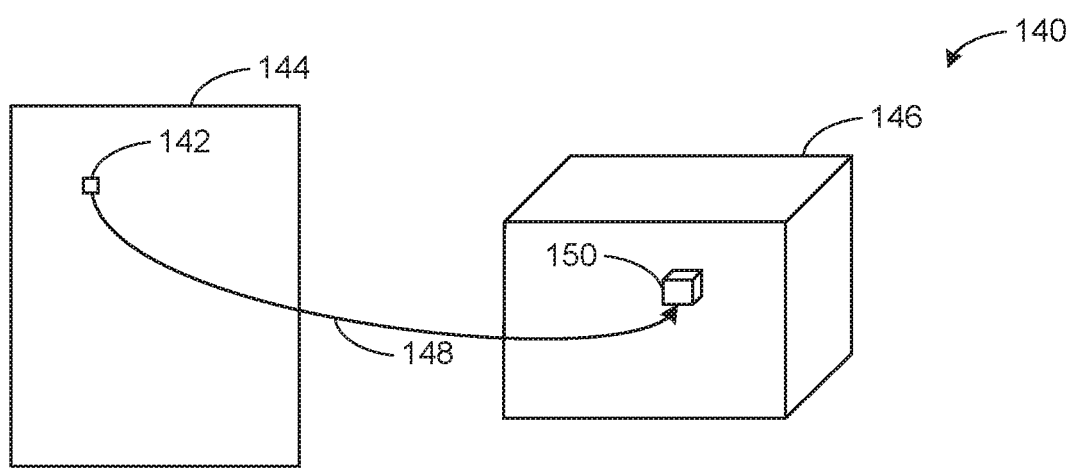
FIG. 1C illustrates an example diagram representing the reconstruction of a pixel using a given volume.

FIG. 1C illustrates an example diagram 140 representing the reconstruction of a pixel 142 within an image 144 using a given volume 146. In this example, the pixel 142 is mapped 148 onto a voxel 150 from the volume according to an acquisition geometry. The view of the pixel 142 in the 2D image 144 is extrapolated to provide a representation of the voxel 150 in the volume 146, for example.

Figure 2A:
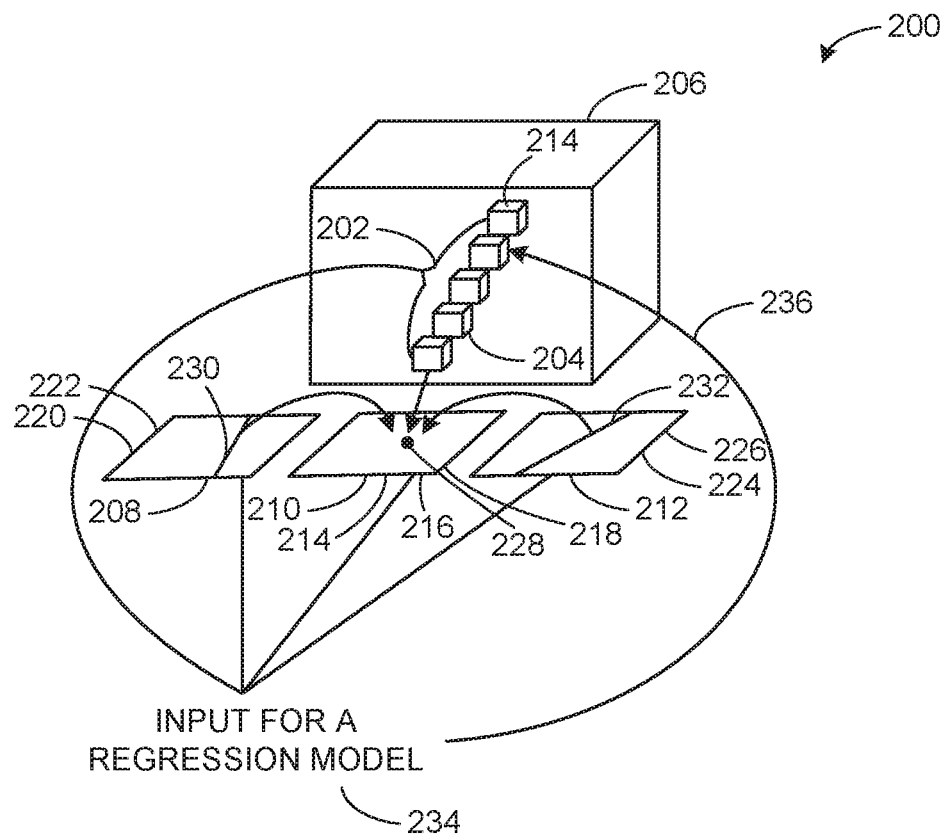
FIG. 2A illustrates an example diagram representing the reconstruction of a slab using imaging projection data.

FIG. 2A illustrates an example diagram 200 representing the reconstruction of a slab 202 using imaging projection data. The slab 202 made of several voxels 204 within a 3D space 206 is to be reconstructed. In this illustrated example, the slab 202 is projected onto a first 2D projected view 208, a second 2D projected view 210, and a third 2D projected view 212, each 2D projected view representing a slice 214 of each voxel 204 in the slab 202. The first 2D projected view 208, the second 2D projected view 210, and the third 2D projected view 212 each have a unique image value and a projected image value. The projected image value 214 of the second 2D projected view 210 is identical to the unique image value 216 because the second 2D projected view 210 contains a base image value 218. In this example, the second 2D projected view 210 contains the base image value 218. However, in other examples, any one of the 2D projected views may contain the base image value. The projected image value 220 of the first 2D projected view 208 represents the distance of the unique image value 222 of the first 2D projected view 208 from the base image value 216. Similarly, the projected image value 224 of the third 2D projected view 212 represents the distance of the unique image value 226 of the third 2D projected view 212 from the base image value 216. For example, if the base image value 216 of the second 2D projection is 8; the unique image value 222 of the first 2D projection 208 is 10; and the unique image value 226 of the third 2D projection 212 is 6, then the projected image value 220 of the first 2D projection 208 is +2 and the projected image value 224 of the third 2D projection 212 is −2. In this example, the unique image values are relatively small, however in other examples they may be much longer which increases computational time and complexity.

Further illustrated in FIG. 2A is a base pixel 228 located in the 2D projected view that contains the base image value 218. In this example, the base pixel 228 is located in the second 2D projected view 210. FIG. 2A also includes lines 230, 232 on each 2D projected view that correspond to other views of the base pixel 228 (e.g., projection images acquired from different angles of the x-ray source with respect to the detector). In this example, the lines 230, 232 are located on the first 2D projected view 208 and the third 2D projected view 212. The lines 230, 232 correspond to the base pixel 228 in the second 2D projected view 210 from different angles. Thus, the pixel 228 can appear as a point in a first view 210 but appear as a line 230, 232 or value with depth in other views 208, 212, for example. These locations can be mapped so that the correspondence is determined when generating a synthetic 2D image, 3D reconstructed image, etc.

Furthermore, in this example, there are only three 2D projected views, while in other examples there may be many more 2D projected views based on how many voxels 204 are in the slab 202, each 2D projected view corresponding to a slice 214 of the voxel 204. This further increases computational time and complexity. By using projected image values instead of unique image values for each 2D projected view, computational time and complexity are decreased. The amount of memory required to store the image values is also decreased.

Further illustrated in FIG. 2 is an input for a regression model 234 provided by the 2D projected views 208, 210, 212. The input for a regression model 234 is then used to reconstruct 236 each voxel 204 within the slab 202 to an approximately identical voxel and, as a result, create an approximately identical slab. The process that the diagram 200 describes repeats until each voxel 204 within the slab 202 has been reconstructed. In this example, the slab 202 that was reconstructed is composed of voxels. However, in other examples, the slab may be composed of any type of graphical element (e.g., pixels, etc.).

Figure 2B:
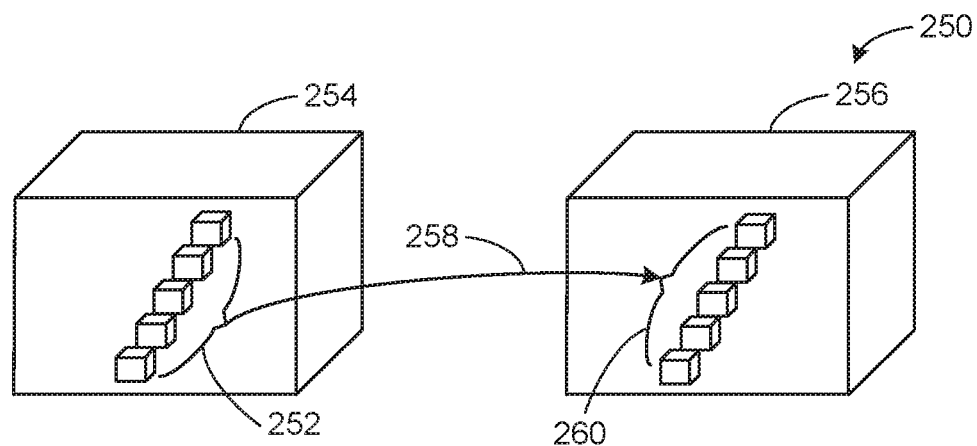
FIG. 2B illustrates an example diagram representing the reconstruction of a slab using a given volume.

FIG. 2B illustrates an example diagram representing the reconstruction of a slab 252 within a 3D space 254 using a given volume 256. While the slab 202 in FIG. 2A is projected onto a set of imaging projections, in this example, the slab 252 is mapped 258 onto the volume 256 to create an approximately identical slab 260.

For example, a 3D geometry can be projected to a 2D surface at a particular viewpoint. Thus, a 3D volume can be represented using a set of 2D views from image projections at different angles of the initial geometry. The 2D projections may include lines that correspond to pixels in other 2D projections.

In certain examples, a point can be selected and/or determined in a view for which a pixel is to be generated, and that point is mapped into a set of pixels in each associated individual view. A point in a target image view can correspond to a line in an adjacent image projection, for example (see, e.g., FIG. 2A in which a point in the central image is a pixel that is mapped to lines in the two other projection views). In a projection image, a pixel is mapped to a voxel used to generate the projection, for example.

Thus, image data with respect an object (e.g., a breast, etc.) can be used to begin with a voxel element of projection to determine where the voxel maps on another projection. In certain examples, beginning with a pixel in an image projection, voxels from which that pixel can originate are determined (e.g., go from projection to volume). In certain examples, starting from a pixel in a first projection, corresponding pixel(s) in other projection(s) can be identified. In certain examples, a voxel can be mapped to voxels in adjacent slices to compute a slab. Thus, a volume can be reconstructed in a 3D image and/or a synthetic 2D image can be created from the projection views and correlations between pixel, voxel, etc.

Figure 3A:
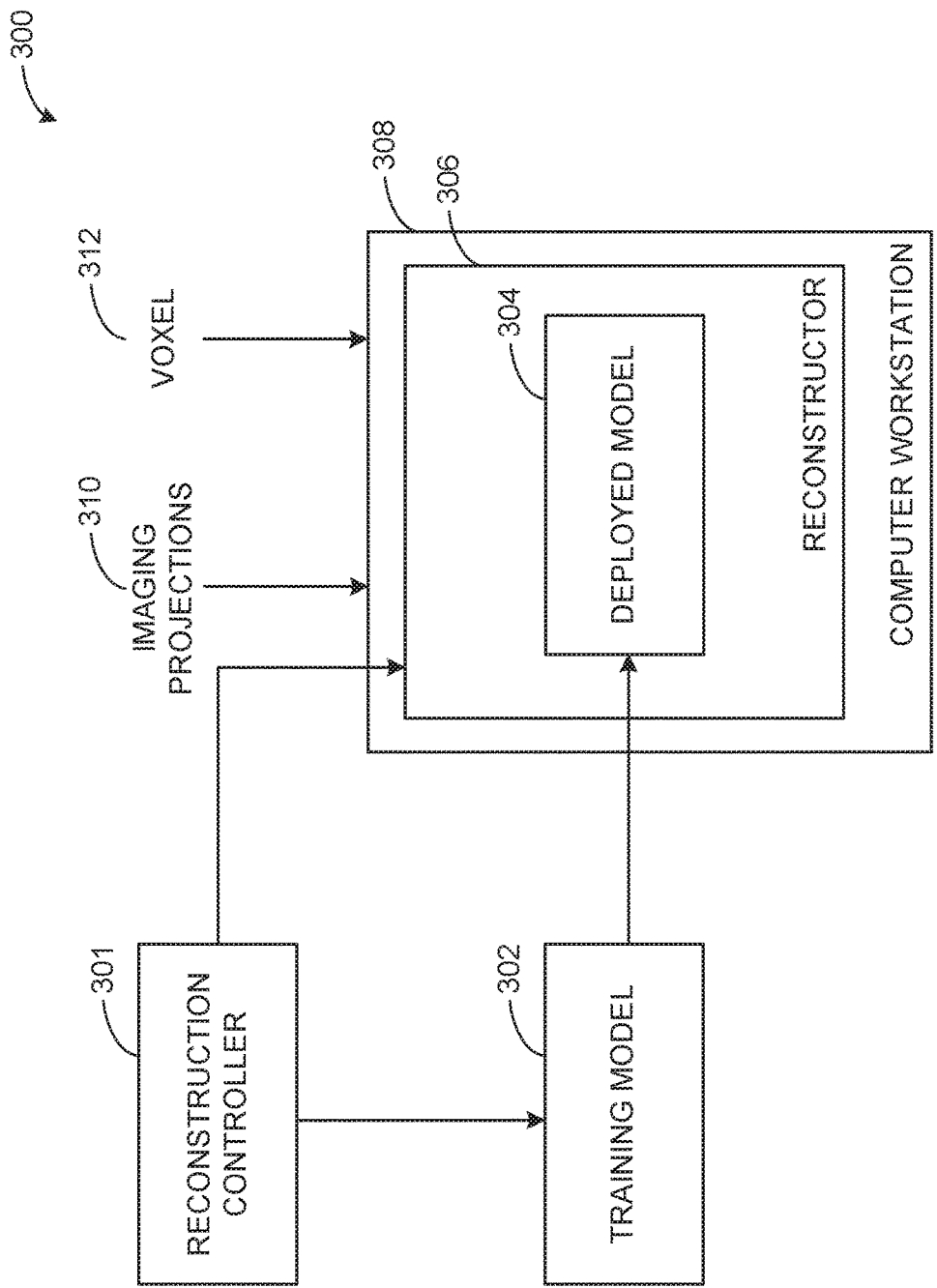
FIG. 3A is a system diagram to implement the diagrams of FIGS. 1A-2B to reconstruct a voxel with imaging projections.
Figure 3B:
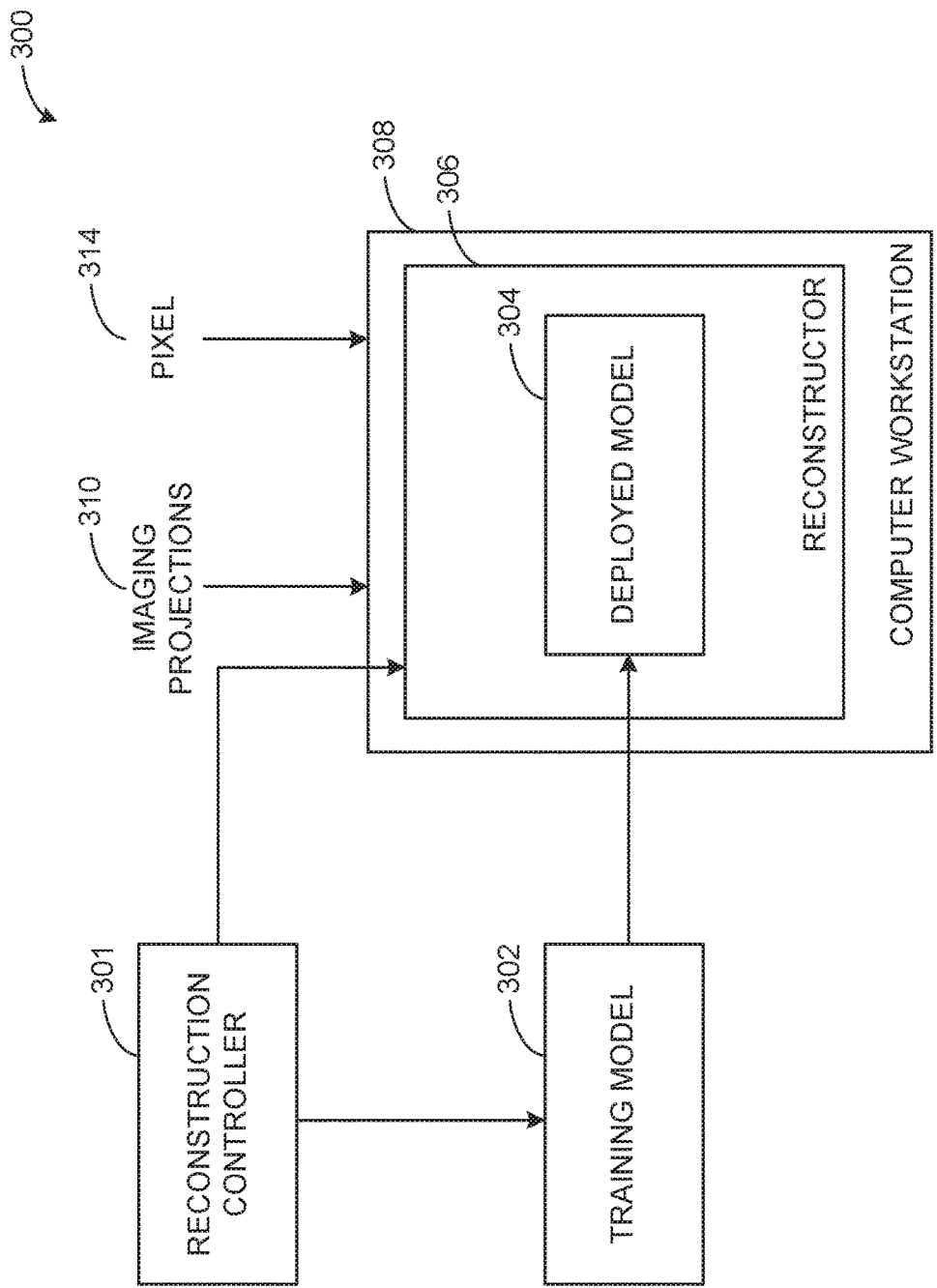
FIG. 3B is a system diagram to implement the diagrams of FIGS. 1A-2B to reconstruct a pixel with imaging projections.
Figure 3C:
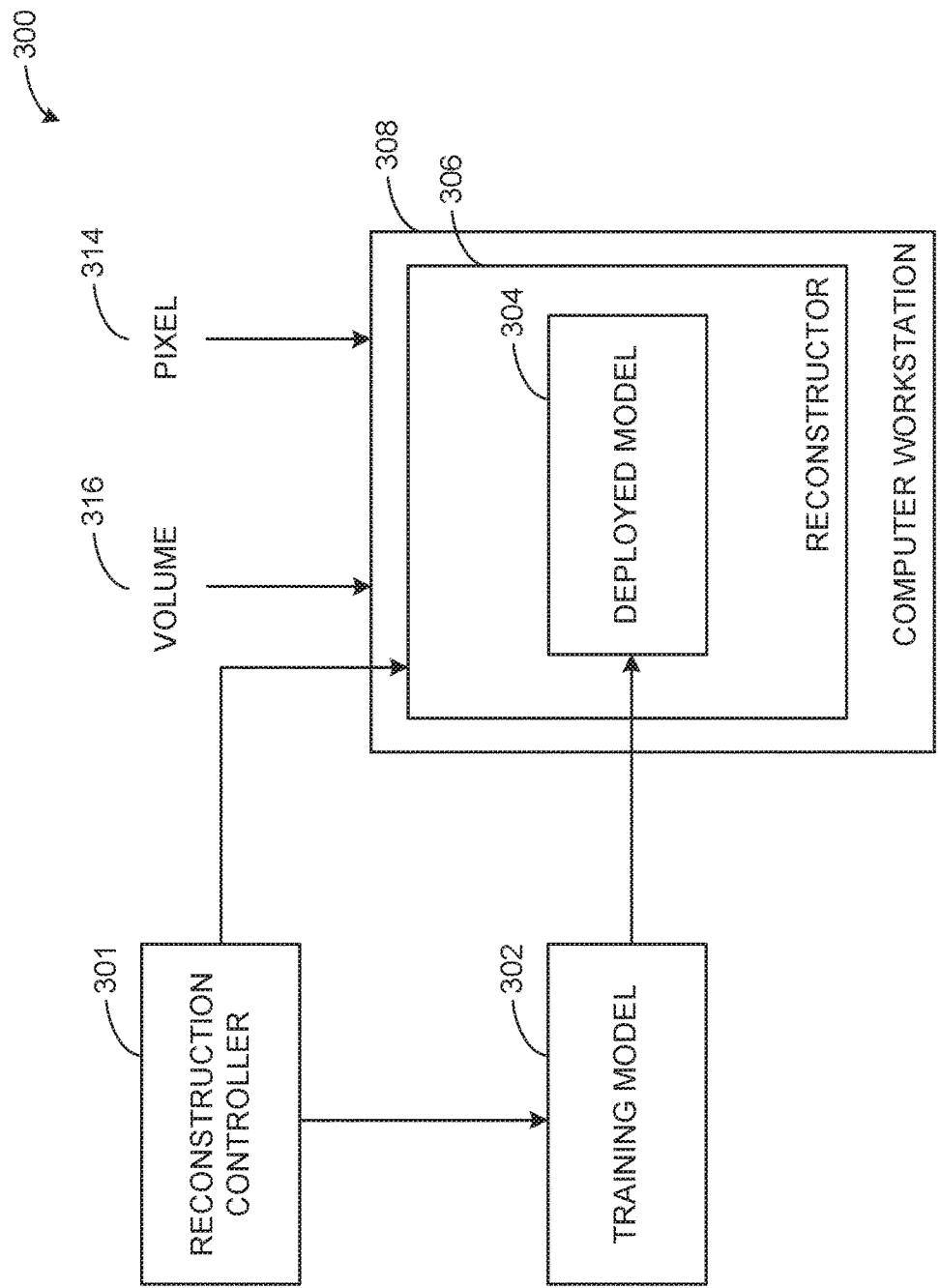
FIG. 3C is a system diagram to implement the diagrams of FIGS. 1A-2B to reconstruct a pixel with a given volume.
Figure 3D:
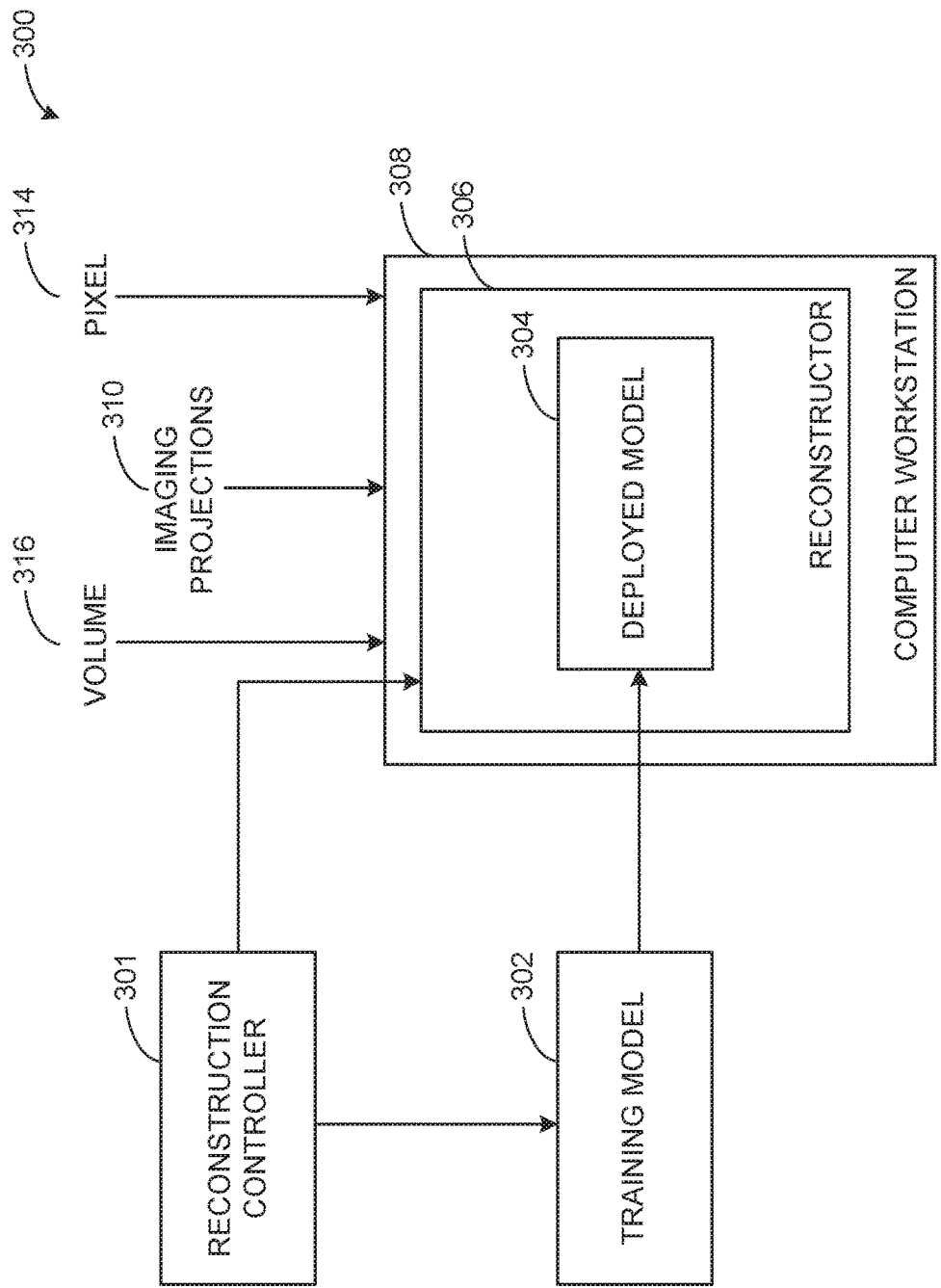
FIG. 3D is a system diagram to implement the diagrams of FIGS. 1A-2B to reconstruct a pixel with imaging projections and a given volume.
Figure 3E:
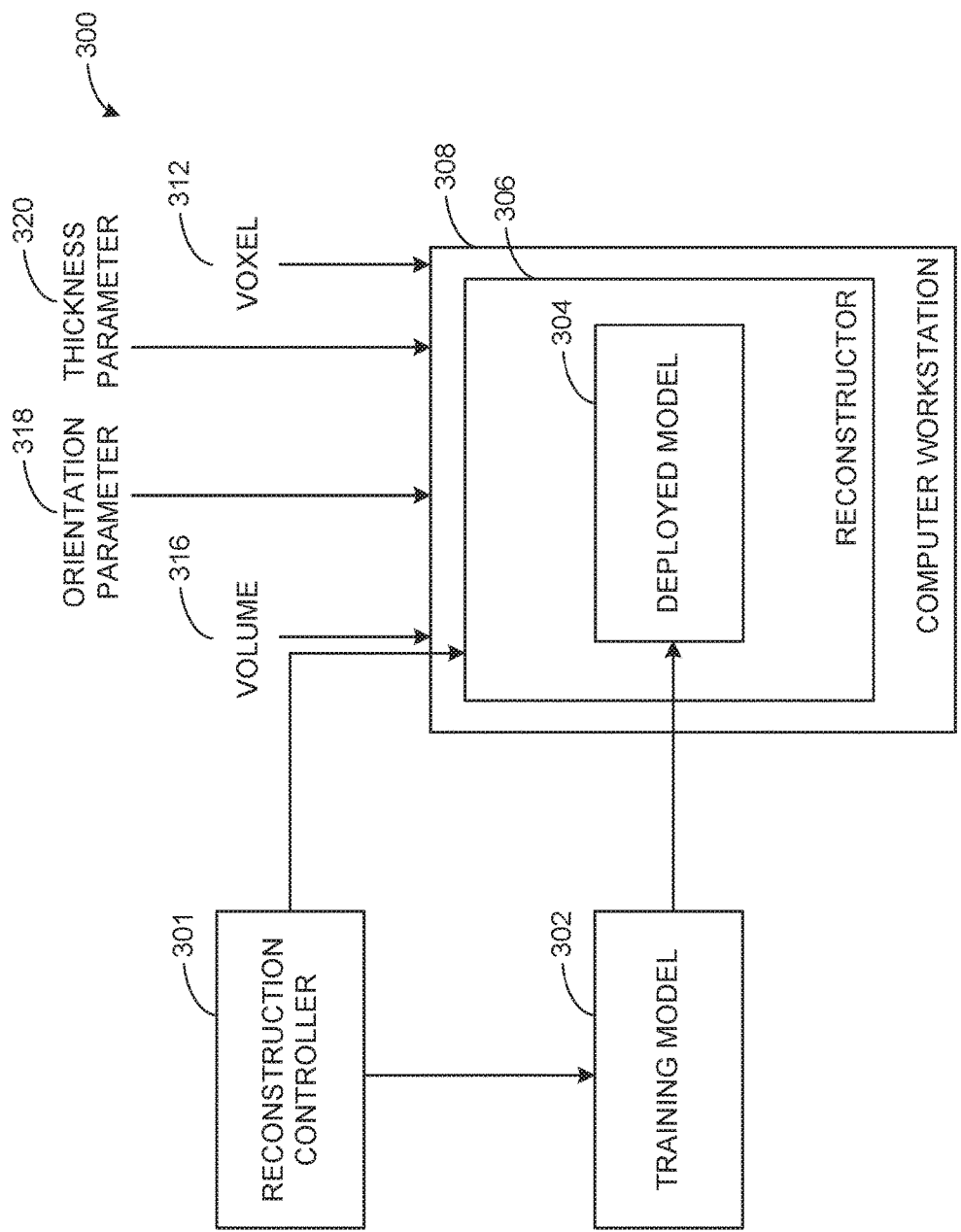
FIG. 3E is a system diagram to implement the diagrams of FIGS. 1A-2B to reconstruct a voxel within a slab with a given volume, a given orientation parameter, and a given thickness parameter.

FIGS. 3A-3E are example systems 300 to reconstruct images such as the examples shown in FIGS. 1A-2B. The example system 300 includes a reconstruction controller 301. The reconstruction controller 301 initiates a reconstruction process such as example process(es) described in further detail below. The reconstruction controller 301 may also decide which method is best to train a regression model at a training model 302 which is described in further detail in FIGS. 4A-4E. The example system 300 further includes a deployed model 304 within a reconstructor 306. The deployed model 304 is a regression model that has been trained at the training model 302. The reconstructor 306 is described in further detail in FIGS. 4A-4E. FIGS. 3A-3E further include a computer workstation 308 encompassing the reconstructor 306 and the deployed model 304. In this example, the training and reconstructing of the regression model are occurring at two different locations. However, in other examples, the training and reconstructing of the regression model may occur at the same location. The computer workstation 308 receives the deployed model 304 from the training model block 302. The computer workstation 308 also receives a pixel, a voxel, and/or a slab to reconstruct, as well as data that is used to reconstruct the pixel, the voxel, and/or the slab. In the example of FIG. 3A, the computer workstation 308 receives imaging projections 310 to reconstruct a voxel 312. In the example of FIG. 3B, the computer workstation 308 receives imaging projections 310 to reconstruct a pixel 314. In the example of FIG. 3C, the computer workstation 308 receives a volume 316 to reconstruct a pixel 314. In the example of FIG. 3D, the computer workstation 308 receives both imaging projections 310 and a volume 316 to reconstruct a pixel 314. In the example of FIG. 3E, the computer workstation 308 receives a volume 316, an orientation parameter 318, and a thickness parameter 320 to reconstruct a voxel 314 that is within a slab. While FIGS. 3A-3E are illustrated separately, in certain examples FIGS. 3A-3E can be combined and implemented as a single system accommodating a plurality of graphic elements such as voxels, pixels, etc., for 2D and/or 3D image generation.

FIGS. 4A-4E illustrate an example implementation of the system 300 of FIGS. 3A-3E described in further detail. The example system 300 includes the reconstruction controller 301 of FIGS. 3A-3E. The example further illustrates a regression model trainer 402 which is located in the training model block 302 of FIGS. 3A-3E. The regression model trainer 402 includes a digital anthropomorphic phantom (DAP) modeler 404, a computed tomography (CT) modeler 406, and an algorithm modifier 408. The DAP modeler 404 includes a DAP acquisition simulator 410, which simulates acquisitions based on digital anthropomorphic phantoms taken from a DAP database 412. The anthropomorphic phantoms act as models of a perfect reconstruction. The DAP modeler further includes a DAP algorithm creator 414, wherein the regression model creates a new algorithm different than existing reconstruction algorithms.

As illustrated in FIGS. 4A-4E, the CT modeler 406 includes a CT acquisition simulator 416, which uses CT reconstructed data as a model of a perfect reconstruction to simulate acquisitions. The CT reconstructed data is stored in a CT database 418 within the CT modeler 406. The CT modeler 406 further includes a CT algorithm creator 420, which allows the regression model to create a new algorithm different than existing reconstruction algorithms based on the CT reconstruction data.

The algorithm modifier 408 of FIGS. 4A-4E includes an algorithm database 422 including acquisitions that have been reconstructed with an algorithm in an algorithm reconstructor 424. The reconstructed algorithm manages noise artifacts in an image to give high image quality. A regression model that is trained in the algorithm modifier 408 decreases computation time and computational complexity of the reconstructed algorithm.

The regression model trainer 402 instructs the DAP modeler 404, the CT modeler 406, and the algorithm modifier 408 to perform the respective training techniques if the appropriate information can be accessed by the respective modeler 404, 406, 408. For example, if the regression model trainer 402 receives a regression model for which only DAPs are available to the regression model trainer 402, then the DAP modeler 404 performs the regression model training. However, in other examples, more than one of the DAP modeler 404, the CT modeler 406, and the algorithm modifier 408 may have information for a given regression model. In such examples, each of the DAP modeler 404, the CT modeler 406, and the algorithm modifier 408 that has the appropriate information performs the regression model training. In such examples, the reconstruction controller 301 can select a result based on one or more criterion such as highest accuracy percentage, fastest response time, etc.

Figure 4A:
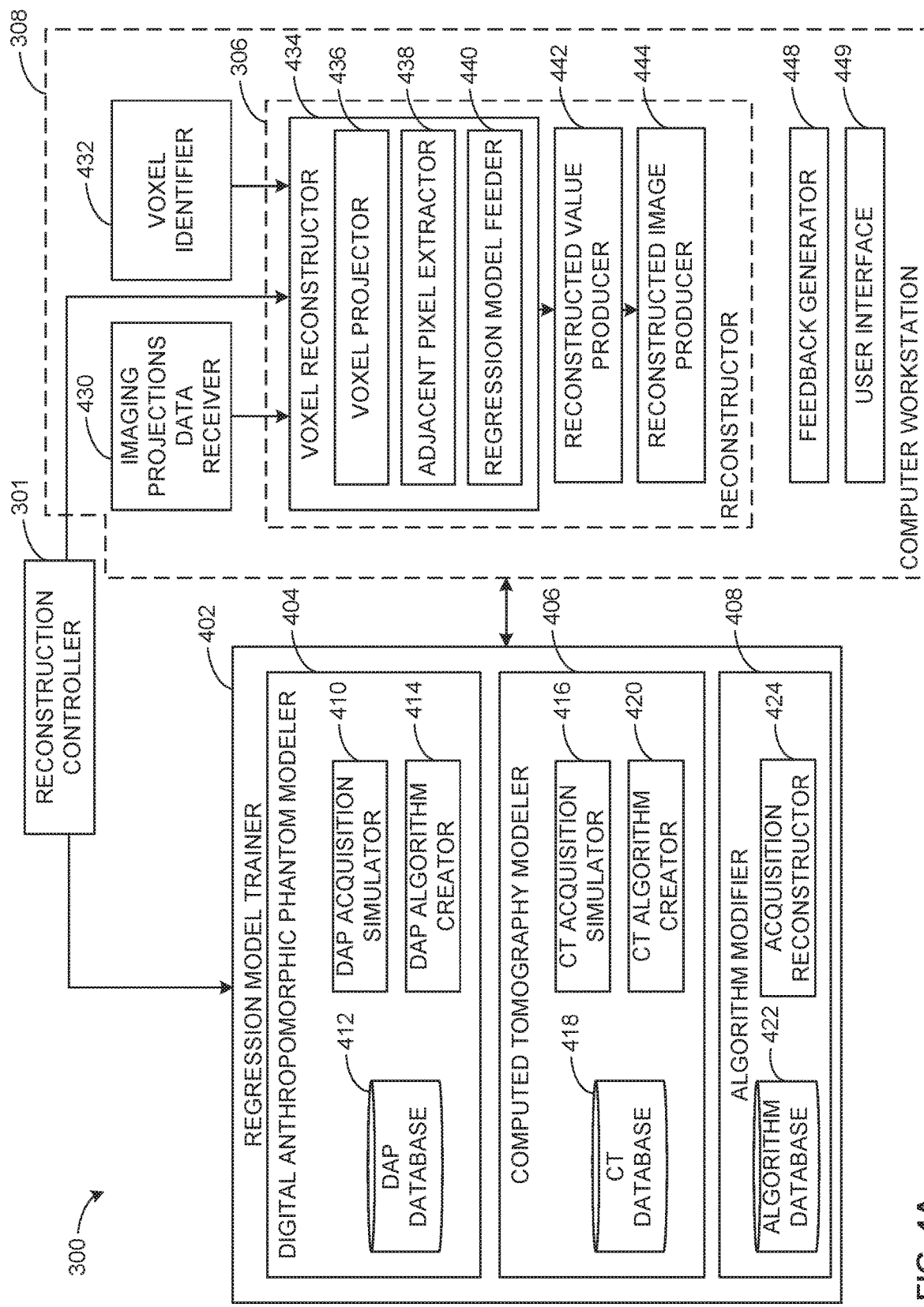
FIG. 4A illustrates an example implementation of the system diagram of FIG. 3A.
Figure 4B:
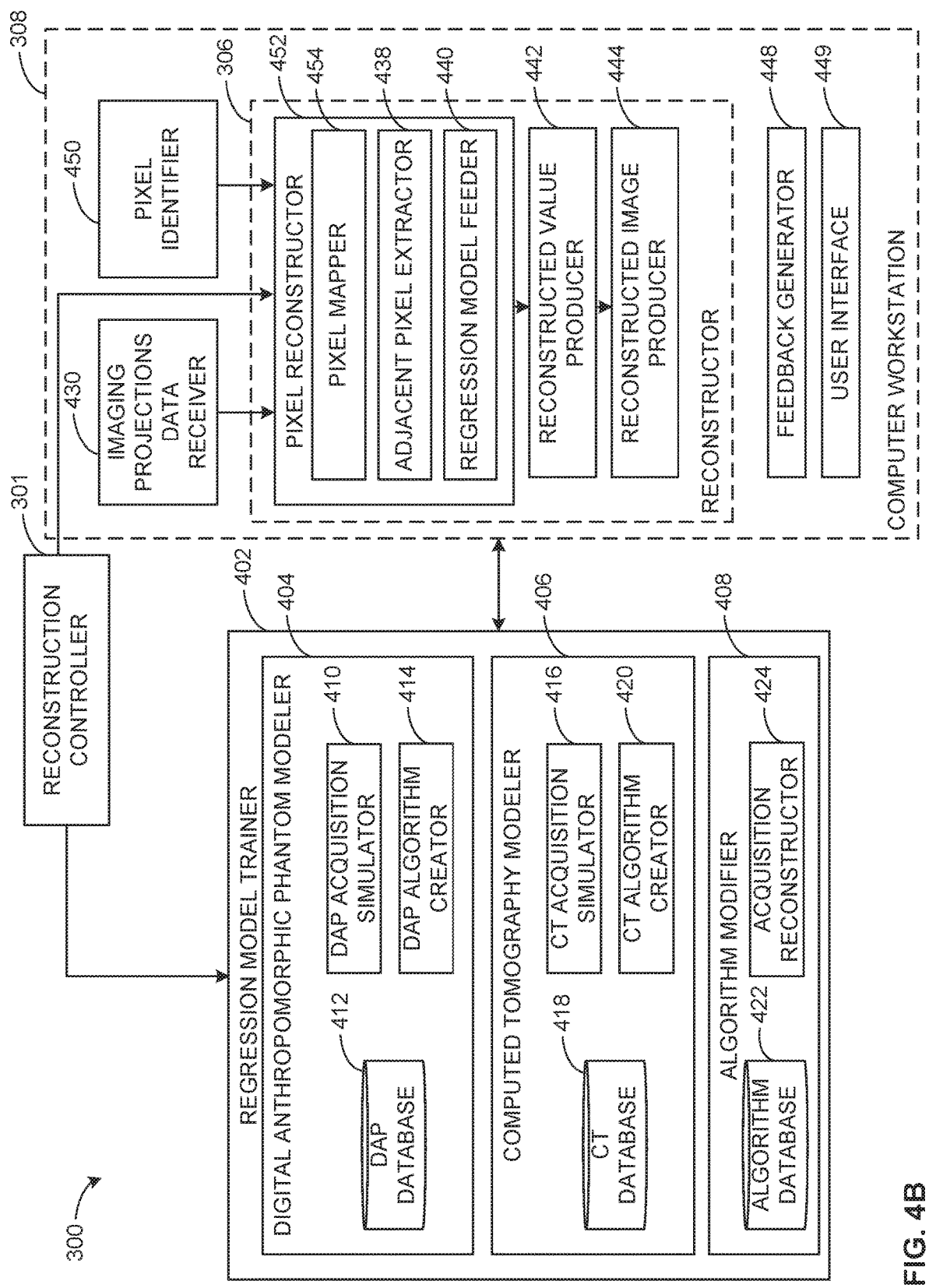
FIG. 4B illustrates an example implementation of the system diagram of FIG. 3B.
Figure 4C:
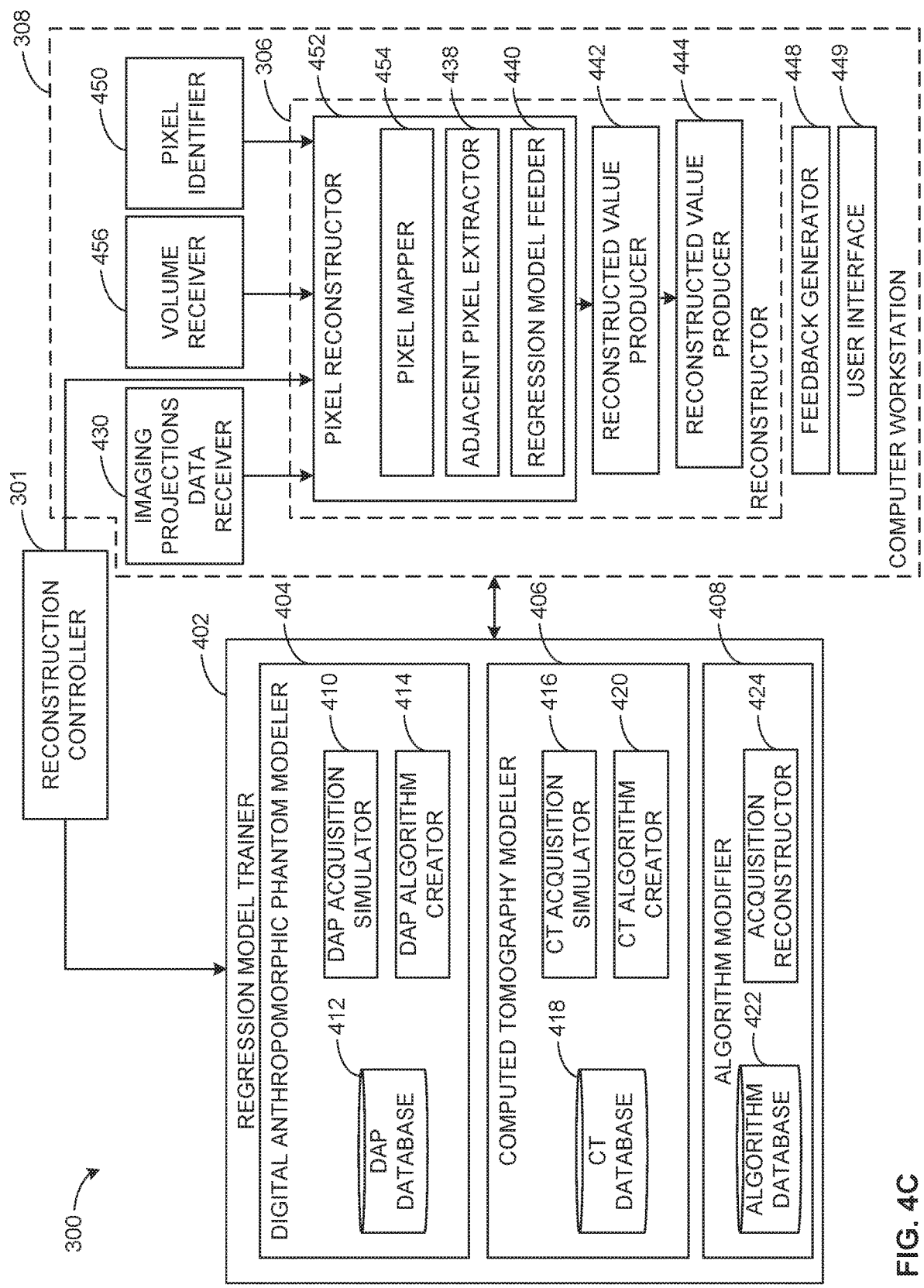
FIG. 4C illustrates an example implementation of the system diagram of FIG. 3C.
Figure 4D:
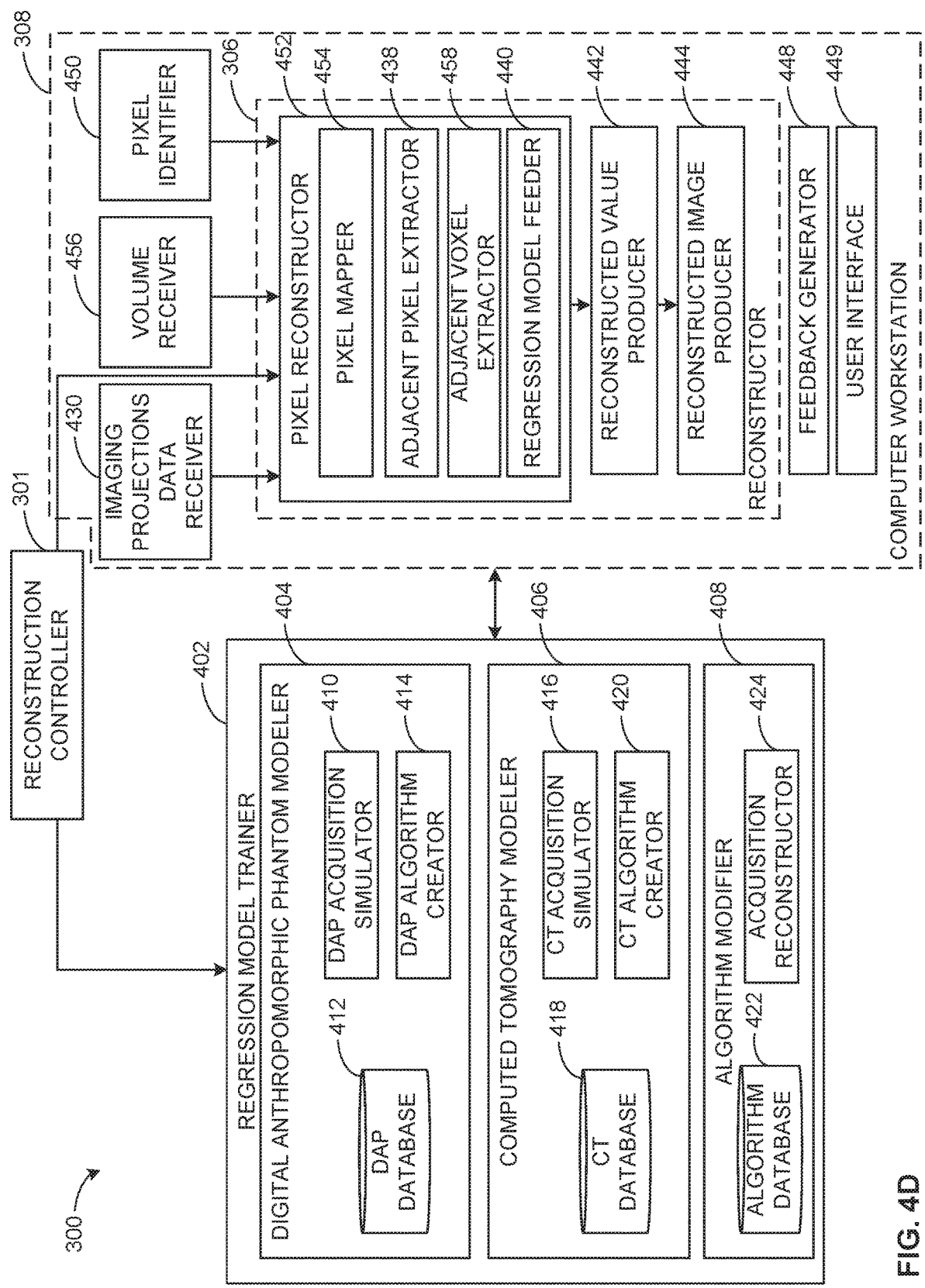
FIG. 4D illustrates an example implementation of the system diagram of FIG. 3D.
Figure 4E:
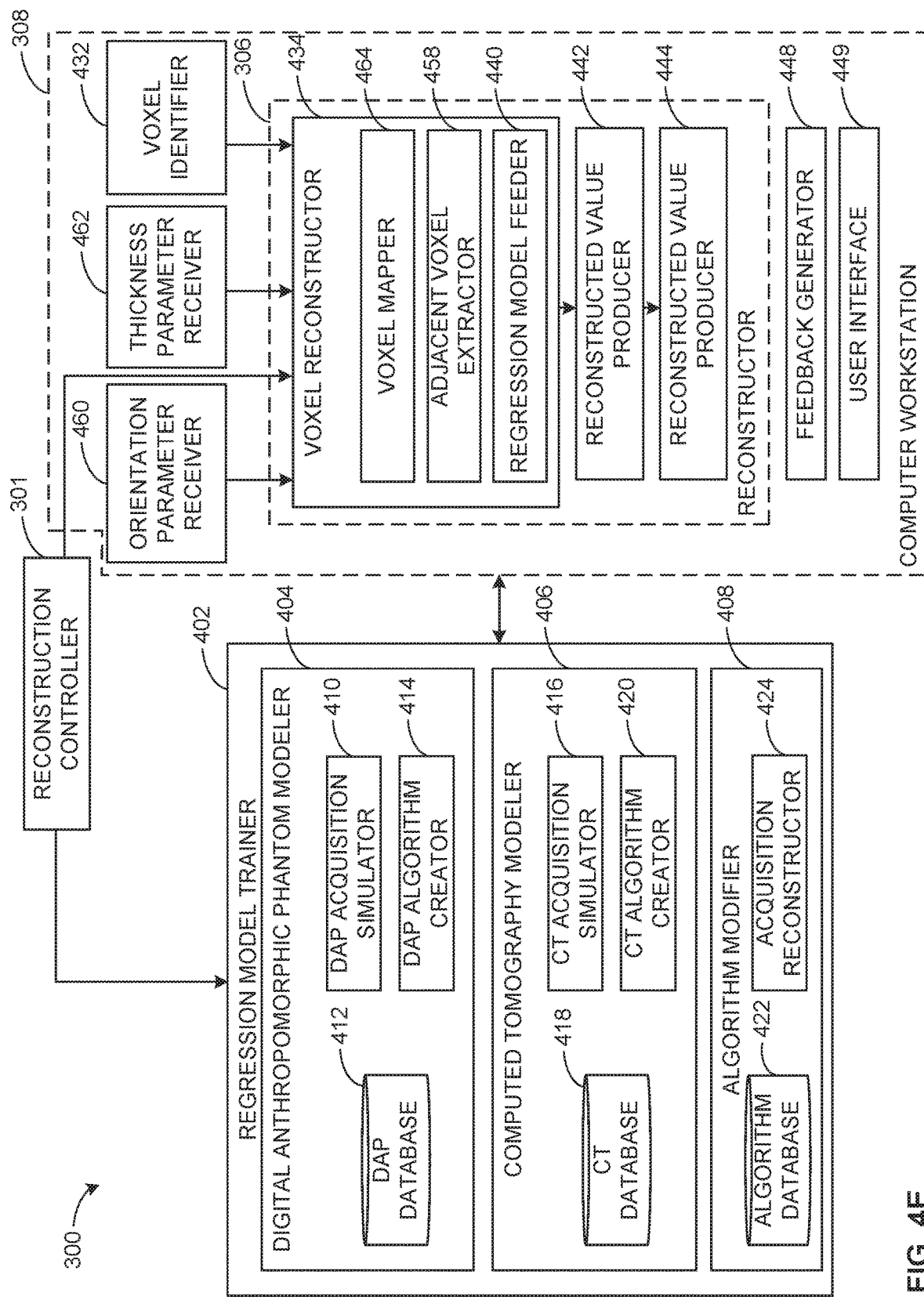
FIG. 4E illustrates an example implementation of the system diagram of FIG. 3E.

Further illustrated in FIGS. 4A-4E is a type of receiver to receive data for reconstruction along with an identifier to identify which element is to be reconstructed. The example of FIG. 4A includes an imaging projections data receiver 430, which receives a set of imaging projections 310 (FIG. 3) and sends the set of imaging projections 310 to a voxel reconstructor 434 located within the reconstructor 306. Further illustrated in FIG. 4A is a voxel identifier 432 to identify the voxel 312 (FIGS. 3A-3E) to be reconstructed and give the voxel 312 to the voxel reconstructor 434. The example of FIG. 4B includes an imaging projections data receiver 430, which receives a set of imaging projections 310 (FIG. 3) and sends the set of imaging projections 310 to a pixel reconstructor 452 located within the reconstructor 306. Further illustrated in FIG. 4A is a pixel identifier 450 to identify the pixel 314 (FIG. 3) to be reconstructed and give the pixel 314 to the pixel reconstructor 452. The example of FIGS. 4C and 4D include an imaging projections data receiver 430, which receives a set of imaging projections 310 (FIG. 3) and sends the set of imaging projections 310 to a pixel reconstructor 452 located within the reconstructor 306. FIGS. 4C and 4D further include a volume receiver 456 to receive the volume 316 and send it to the pixel reconstructor 452. Further illustrated in FIGS. 4C and 4D is a pixel identifier 450 to identify the pixel 314 (FIG. 3) to be reconstructed and give the pixel 314 to the pixel reconstructor 452. The example of FIG. 4E includes an orientation parameter receiver 460 to receive the orientation parameter 318 and a thickness parameter receiver 462 to receive the thickness parameter 320. The orientation parameter 318 and the thickness parameter 320 are sent to a voxel reconstructor 434. Further illustrated in FIG. 4E is a voxel identifier 432 to identify the voxel 312 (FIG. 3) to be reconstructed and give the voxel 312 to the voxel reconstructor 434.

The reconstructor 306 of FIGS. 4A-4E includes elements to reconstruct the given voxel 312 or pixel 314. The voxel reconstructor 434 of FIG. 4A includes a voxel projector 436 to project the voxel 312 on each of the set of 2D projections 208, 210, 212 of FIG. 2 according to an acquisition geometry; an adjacent pixel extractor 438 to extract adjacent pixels around each projected voxel 312; and a regression model feeder 440 to feed the regression model with the extracted adjacent pixel data. The pixel reconstructor 452 of FIGS. 4B and 4C includes a pixel mapper 454 to map the pixel 314 onto each imaging projection of the set of projections according to an acquisition geometry; an adjacent pixel extractor 438 to extract adjacent pixels around each mapped pixel 314; and a regression model feeder 440 to feed the regression model with the extracted adjacent pixel data. The pixel reconstructor 452 of FIG. 4D includes a pixel mapper 454 to map the pixel 314 onto each imaging projection of the set of projections according to an acquisition geometry; an adjacent pixel extractor 438 to extract adjacent pixels around each mapped pixel 314 in the projections; an adjacent voxel extractor 458 to extract adjacent voxels around each mapped pixel 314 in a volume; and a regression model feeder 440 to feed the regression model with the extracted adjacent pixel data and extracted adjacent voxel data. The voxel reconstructor 434 of FIG. 4E includes a voxel mapper 464 to map the voxel 312 onto voxels from the volume 316 according to the orientation parameter 318 and the thickness parameter 320 of the slab from which the voxel 312 originated; an adjacent voxel extractor 458 to extract adjacent voxels around each mapped voxel 312; and a regression model feeder 440 to feed the regression model with the extracted adjacent voxel data. The data from the either voxel reconstructor 434 or the pixel reconstructor 452 of FIGS. 4A-4E is sent to a reconstructed value producer 442 which produces a reconstructed value of the reconstructed pixel or the reconstructed voxel (e.g., a gray value, etc.). The reconstructed value is received by a reconstructed image producer 444, which produces a reconstructed image based on the reconstructed values. The imaging projections data receiver 430, the volume receiver 456, the voxel identifier 432, the pixel identifier 450, the orientation parameter receiver 460, the thickness parameter receiver, the voxel reconstructor 434, the pixel reconstructor 452, the reconstructed value producer 442, and the reconstructed image producer 444 are part of the computer workstation 308 of FIG. 3.

The computer workstation 308 also includes a feedback generator 448. The feedback generator 448 identifies if a possible mistake has been made in the reconstructed image . . . . The reconstructed image producer 444 sends the reconstructed image to the user interface for a user to view. For example, if every reconstructed graphical element 312 within a reconstructed image is a dark color except one outlier that is a light or bright color, the disparity in color/intensity may be an indication of a mistake made by either the regression model trainer 402 or the reconstructor 306. In such examples, the feedback generator 448 communicates to the regression model trainer 402 to choose a different method of the DAP modeler 404, the CT modeler 406, and the algorithm modifier 408 to re-train the regression model. For example, if a regression model was trained using DAPs in the DAP modeler 404 the feedback generator 448 indicates that a mistake may have been made, then the feedback generator 448 communicates to the regression model trainer 402 that the regression model is to be re-trained on either the CT modeler 406 or the algorithm modifier 408. In such an example, the accuracy percentage for the DAP modeler 404 would decrease. As a result, the reconstruction controller 301 may be less likely to select the DAP modeler 404 to train a regression model if the regression model trainer 402 has information for more than one method to train the regression model.

The computer workstation 308 further includes a user interface 449. The reconstructed image producer 444 sends the reconstructed image to the user interface 449 to be viewed by a user. In some examples, the reconstructed image may not be available to the user until the feedback generator 448 decides that there are not any mistakes within the reconstructed image. However, in other examples, the user interface 449 may display the reconstructed image immediately after it is produced by the reconstructed image producer 444. In such examples, if the feedback generator 448 indicates that a mistake has been made, the user interface 449 may display the first reconstructed image until the second, more accurate, reconstructed image has been produced.

While an example manner of implementing the example system 300 of FIGS. 4A-4E is illustrated in FIGS. 5-12, one or more of the elements, processes and/or devices illustrated in FIGS. 3A-4E may be combined, divided, re-arranged, omitted, eliminated and/or implemented in any other way. For example, while FIGS. 4A-4E are illustrated separately, in certain examples FIGS. 4A-4E can be combined and implemented as a single system accommodating a plurality of graphic elements such as voxels, pixels, etc., for 2D and/or 3D image generation. Further, the example reconstruction controller 301, the example regression model trainer 402 which can, in some examples, contain the example digital anthropomorphic phantom modeler 404 which can, in some examples, contain the example DAP acquisition simulator 410, the example DAP database 412, and the example algorithm creator 414; the example CT modeler 406 which can, in some examples contain the example CT acquisition simulator 416, the example CT database 418, and the example CT algorithm creator 420; the example algorithm modifier 408 which can, in some examples contain the example algorithm database 422 and the example acquisition reconstructor 424; the example imaging projections data receiver 430, the example volume receiver 456, the example orientation parameter receiver 460, the example thickness parameter receiver 462, the example pixel identifier 450, the example voxel identifier 432, the example reconstructor 306 which can, in some examples include the example voxel reconstructor 434 which can, in some examples, contain the example voxel projector 436, the example adjacent pixel extractor 438, the example regression model feeder 440, the example voxel mapper 464, and the example adjacent voxel extractor 458; the example pixel reconstructor 452 which can, in some examples, contain the example pixel mapper 454, the example adjacent pixel extractor 438, the example regression model feeder 440, and the example adjacent voxel extractor 458; the example reconstructed value producer 442, and the example feedback generator 448 and/or, more generally, the example system 300 of FIGS. 4A-4E may be implemented by hardware, software, firmware and/or any combination of hardware, software and/or firmware. Thus, for example, any of the example reconstruction controller 301, the example regression model trainer 402 which can, in some examples, contain the example digital anthropomorphic phantom modeler 404 which can, in some examples, contain the example DAP acquisition simulator 410, the example DAP database 412, and the example algorithm creator 414; the example CT modeler 406 which can, in some examples contain the example CT acquisition simulator 416, the example CT database 418, and the example CT algorithm creator 420; the example algorithm modifier 408 which can, in some examples contain the example algorithm database 422 and the example acquisition reconstructor 424; the example imaging projections data receiver 430, the example volume receiver 456, the example orientation parameter receiver 460, the example thickness parameter receiver 462, the example pixel identifier 450, the example voxel identifier 432, the example reconstructor 306 which can, in some examples include the example voxel reconstructor 434 which can, in some examples, contain the example voxel projector 436, the example adjacent pixel extractor 438, the example regression model feeder 440, the example voxel mapper 464, and the example adjacent voxel extractor 458; the example pixel reconstructor 452 which can, in some examples, contain the example pixel mapper 454, the example adjacent pixel extractor 438, the example regression model feeder 440, and the example adjacent voxel extractor 458; the example reconstructed value producer 442, the example reconstructed image producer 444, the example feedback generator 448 and/or, more generally, the example system 300 of FIGS. 4A-4E can be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example reconstruction controller 301, the example regression model trainer 402 which can, in some examples, contain the example digital anthropomorphic phantom modeler 404 which can, in some examples, contain the example DAP acquisition simulator 410, the example DAP database 412, and the example algorithm creator 414; the example CT modeler 406 which can, in some examples contain the example CT acquisition simulator 416, the example CT database 418, and the example CT algorithm creator 420; the example algorithm modifier 408 which can, in some examples contain the example algorithm database 422 and the example acquisition reconstructor 424; the example imaging projections data receiver 430, the example volume receiver 456, the example orientation parameter receiver 460, the example thickness parameter receiver 462, the example pixel identifier 450, the example voxel identifier 432, the example reconstructor 306 which can, in some examples include the example voxel reconstructor 434 which can, in some examples, contain the example voxel projector 436, the example adjacent pixel extractor 438, the example regression model feeder 440, the example voxel mapper 464, and the example adjacent voxel extractor 458; the example pixel reconstructor 452 which can, in some examples, contain the example pixel mapper 454, the example adjacent pixel extractor 438, the example regression model feeder 440, and the example adjacent voxel extractor 458; the example reconstructed value producer 442, the example reconstructed image producer 444, and the example feedback generator 448 and/or, more generally, the example system 300 of FIGS. 4A-4E is/are hereby expressly defined to include a tangible computer readable storage device or storage disk such as a memory, a digital versatile disk (DVD), a compact disk (CD), a Blu-ray disk, etc. storing the software and/or firmware. Further still, the example system 300 of FIGS. 4A-4E may include one or more elements, processes and/or devices in addition to, or instead of, those illustrated in FIGS. 4A-4E, and/or may include more than one of any or all of the illustrated elements, processes and devices.

A flowchart representative of example machine readable instructions for implementing the example system 300 of FIGS. 4A-4E is shown in FIGS. 5-12. In this example, the machine readable instructions comprise a program for execution by a processor such as the processor 1312 shown in the example processor platform 1300 discussed below in connection with FIGS. 5-12. The program may be embodied in software stored on a tangible computer readable storage medium such as a CD-ROM, a floppy disk, a hard drive, a digital versatile disk (DVD), a Blu-ray disk, or a memory associated with the processor 1312, but the entire program and/or parts thereof could alternatively be executed by a device other than the processor 1312 and/or embodied in firmware or dedicated hardware. Further, although the example program is described with reference to the flowchart illustrated in FIGS. 5-12, many other methods of implementing the example system 300 may alternatively be used. For example, the order of execution of the blocks may be changed, and/or some of the blocks described may be changed, eliminated, or combined.

As mentioned above, the example processes of FIGS. 5-12 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIGS. 5-12 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

Figure 5:
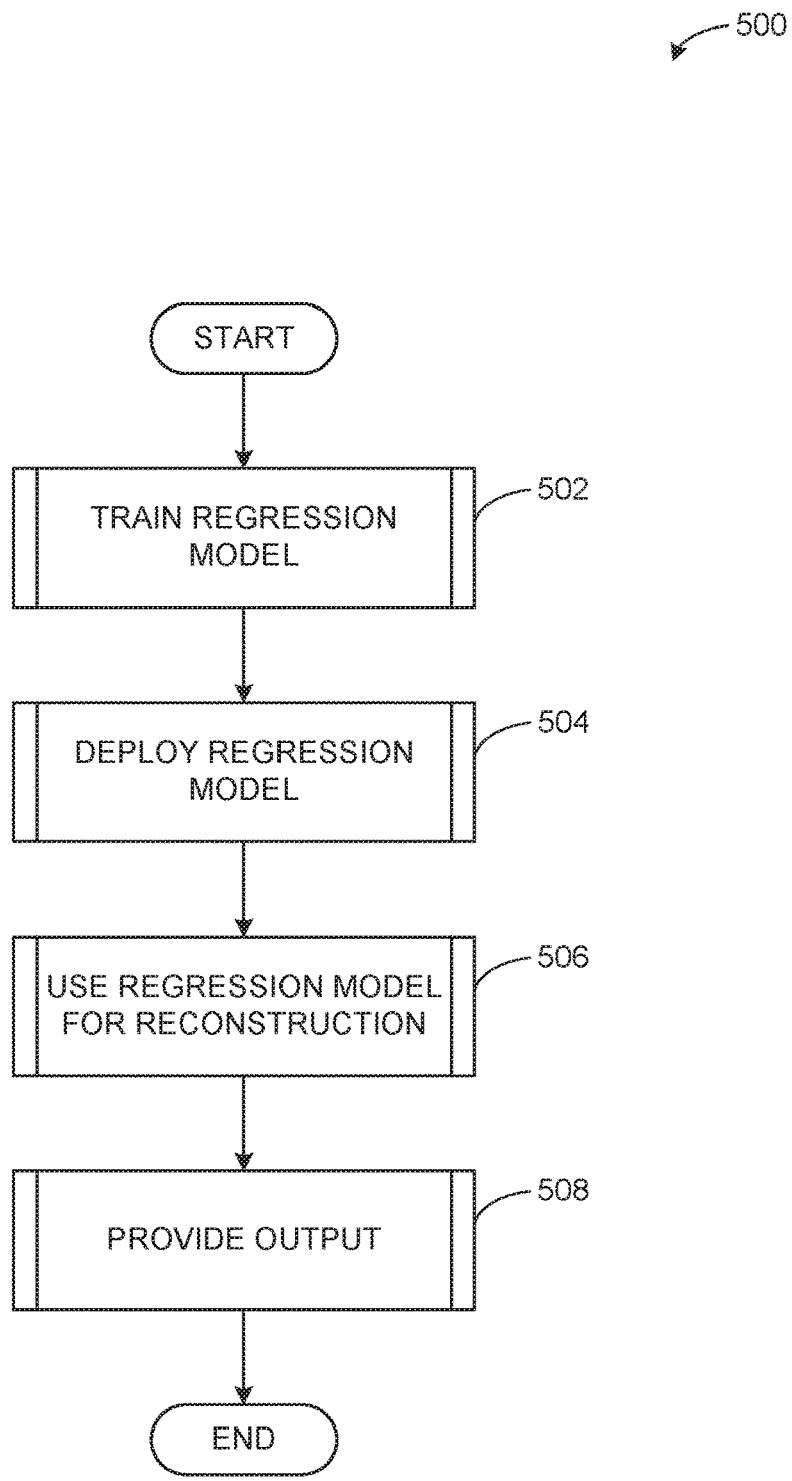
FIG. 5 is a flowchart representative of an example method to reconstruct an image.

FIG. 5 is a flowchart representative of an example method 500 to produce a reconstructed image. The example method 500 begins at block 502 where the regression model trainer 402 trains a regression model. For example, to reconstruct a digital breast tomosynthesis (DBT) projection, the process starts with the regression model trainer 402 training a regression model. At block 504, the regression model trainer 402 (FIGS. 4A-4E) deploys the regression model. In this example, after the regression model has been trained, the regression model is deployed to the voxel reconstructor 434 or the pixel reconstructor 452. DBT projections data and a voxel 312 or a pixel 314 (FIGS. 3A-3E) are also sent to the voxel reconstructor 434 or the pixel reconstructor 452. At block 506, the voxel reconstructor 434 or the pixel reconstructor 452 uses the regression model for reconstruction. In the illustrated example, the voxel reconstructor 434 or the pixel reconstructor 452 uses the deployed regression model and the DBT projections data to reconstruct the voxel 312 or the pixel 314 sent by the voxel identifier 432 or the pixel identifier 450 (FIGS. 4A-4E). At block 508, the reconstructed value producer 442 provides an output of a reconstructed image value. For example, the reconstructed value producer 442 (FIGS. 4A-4E) produces a reconstructed image value of the breast from the DBT projections data. Example implementations of blocks 502, 504, 506, 508, are described in more detail below.

Figure 6:
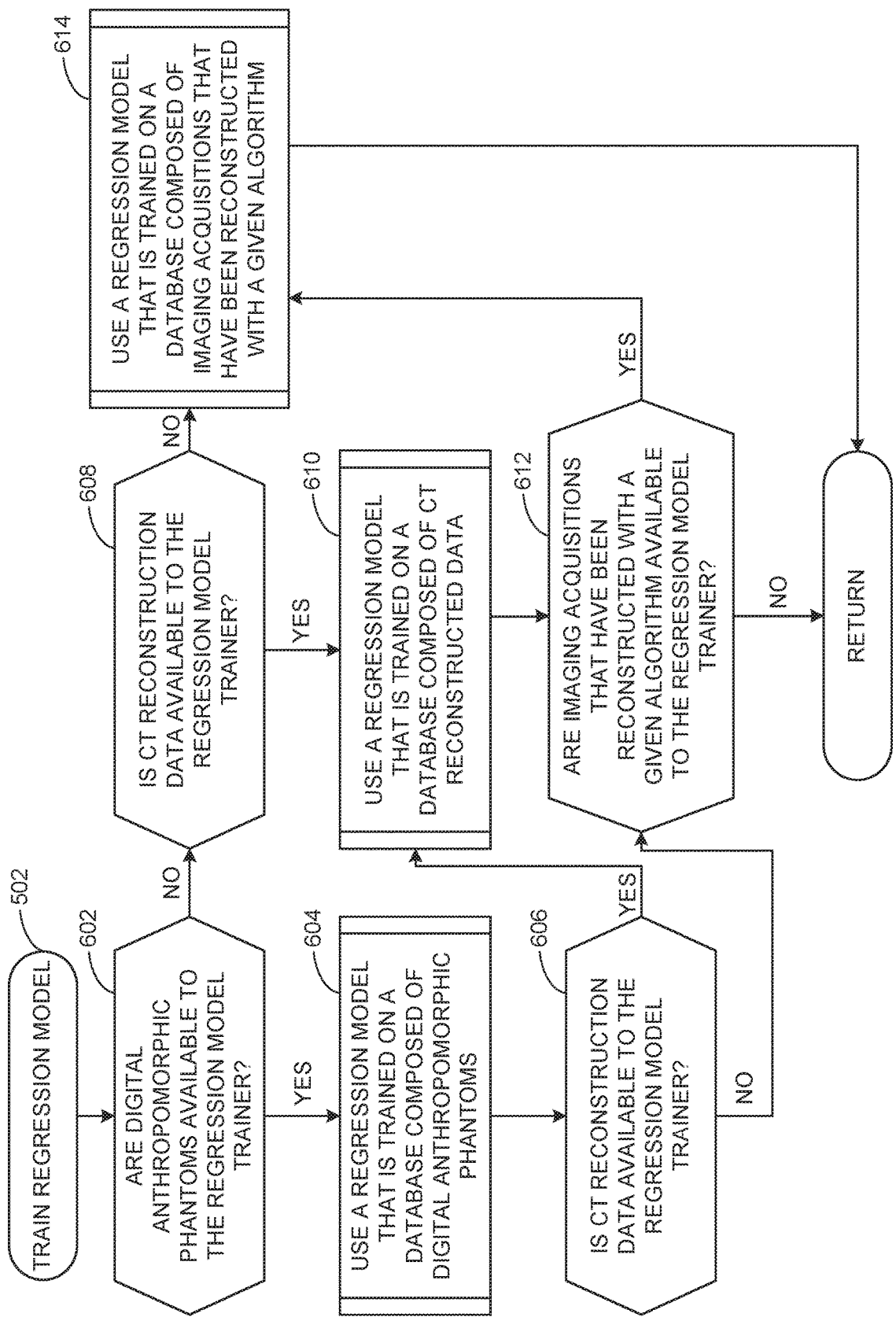
FIG. 6 is a flowchart representative of an example method to choose a training method to train a regression model.

FIG. 6 is a flowchart representative of an example implementation of training a regression model (block 502 of FIG. 5). At block 602, the regression model trainer 402 determines if digital anthropomorphic phantoms (DAPs) are available to the regression model trainer 402. If DAPs are available to the regression model trainer 402 at block 604, the regression model trainer 402 is instructed to train the regression model on the DAP modeler 404 using a database composed of DAPs. An example of training a regression model on the DAP modeler 404 is further described with respect to FIG. 7. In some examples, if the regression model trainer has DAPs for a regression model, then the regression model is trained on the DAP modeler 404. In these examples, the regression model trainer 402 checks for DAPs first. However, in other examples, the regression model trainer 402 may check for CT reconstruction data or imaging acquisitions that have been reconstructed with a given algorithm before checking for DAPs.

After the regression model trainer 402 is instructed to utilize the DAP modeler 404, or if DAPs were not available at block 602, then at blocks 606 and 608 respectively, the regression model trainer 402 is instructed to determine if computed tomography (CT) data is available. If CT data is available, then, at block 610, the regression model trainer 402 is instructed to train the regression model on the CT modeler 406 using a database composed of CT reconstruction data. An example of training a regression model on a database composed of CT reconstruction data is further described with respect to FIG. 8. In some examples, the regression model trainer 402 may have DAPs available to train a regression model. In such examples, after the regression model trainer 402 instructs the DAP modeler 404 to train the regression model (block 604), the regression model trainer 402 checks if there is CT reconstruction data available to train the regression model (block 606). If CT reconstruction data is available, the regression model is trained on the CT modeler 406 (block 610). In further examples, the regression model trainer 402 may not have had DAPs available to train a regression model. In such examples, the regression model trainer checks if there is CT reconstruction data available to train the regression model (block 608). If CT reconstruction data is available, the regression model is trained on the CT modeler 406 (block 610). In these illustrated examples, the regression model trainer 402 checks for CT reconstruction data (blocks 606, 608) after the regression model trainer 402 checks for DAPs (block 602) and before the regression model trainer 402 checks for imaging acquisitions that have been reconstructed with a given algorithm (block 612). However, in other examples, the regression model trainer 402 may check for CT reconstruction data first or last.

After the regression model trainer 402 is instructed to train the regression model using the CT modeler 406 (block 610); or if CT reconstruction data was not available, but DAPs were available at block 602, then the regression model trainer 402 determines if imaging acquisitions that have been reconstructed with a given algorithm are available at block 612. If imaging acquisitions that have been reconstructed with a given algorithm are available, and/or if neither DAPs nor CT reconstruction data were available at blocks 602 and 608 respectively, then, at block 614, the regression model trainer 402 is instructed to use a regression model that is trained on the algorithm modifier 408 using a database composed of imaging acquisitions that have been reconstructed with a given algorithm. An example of training a regression model on the algorithm modifier 408 is further described with respect to FIG. 9. In some examples, the regression model trainer 402 has access to CT reconstruction data. In such examples, after the regression model trainer 402 is instructed to use the CT modeler 406 to train the regression model (block 610), the regression model trainer 402 determines if imaging acquisitions that have been reconstructed with a given algorithm are available (block 612). If imaging acquisitions that have been reconstructed with a given algorithm are available, then the regression model trainer 402 trains the regression model on the algorithm modifier 408 (block 614). In further examples, the regression model trainer 402 may not have access to CT reconstruction data, but does have access to DAPs. In these examples, after instructing the DAP modeler 404 to train the regression model (block 606) and after confirming that CT reconstruction data is unavailable, the regression model trainer 402 determines if imaging acquisitions that have been reconstructed with a given algorithm are available (block 612). If imaging acquisitions that have been reconstructed with a given algorithm are available, then the regression model trainer 402 trains the regression model on the algorithm modifier 408 (block 614). In even further examples, the regression model trainer 402 may not have had access to CT reconstruction data or DAPs. In such examples, the regression model trainer 402 automatically instructs the algorithm modifier 408 to train the regression model (block 614). In these examples, the assumption is made that if a regression model is received by the regression model trainer 402, then the regression model trainer 402 also receives at least one of DAPs, CT reconstruction data, or imaging acquisitions that have been reconstructed using a given algorithm. However, in other examples, the regression model trainer 402 may not receive any of the DAPs, CT reconstruction data, or the imaging acquisitions that have been reconstructed using a given algorithm. In such examples, an error message shows on the user interface 449 of FIGS. 4A-4E as the regression model cannot be trained.

After the regression model trainer 402 is instructed to train the regression model on the algorithm modifier 408 (block 614), the process returns to block 504 of FIG. 5. Additionally, if DAPs and/or CT reconstruction data are available, but imaging acquisitions that have been reconstructed with a given algorithm are not available, then the process returns to block 504 of FIG. 5. For example, if the regression model trainer 402 instructs the algorithm modifier 408 to train the regression model, then the process returns to block 504 of FIG. 5. In further examples, if the regression model trainer 402 instructs the DAP modeler 404 and/or the CT modeler 406 to train the regression model, but imaging acquisitions that have been reconstructed with a given algorithm are not available to the regression model trainer 402, then the program returns to block 504 of FIG. 5.

Figure 7:
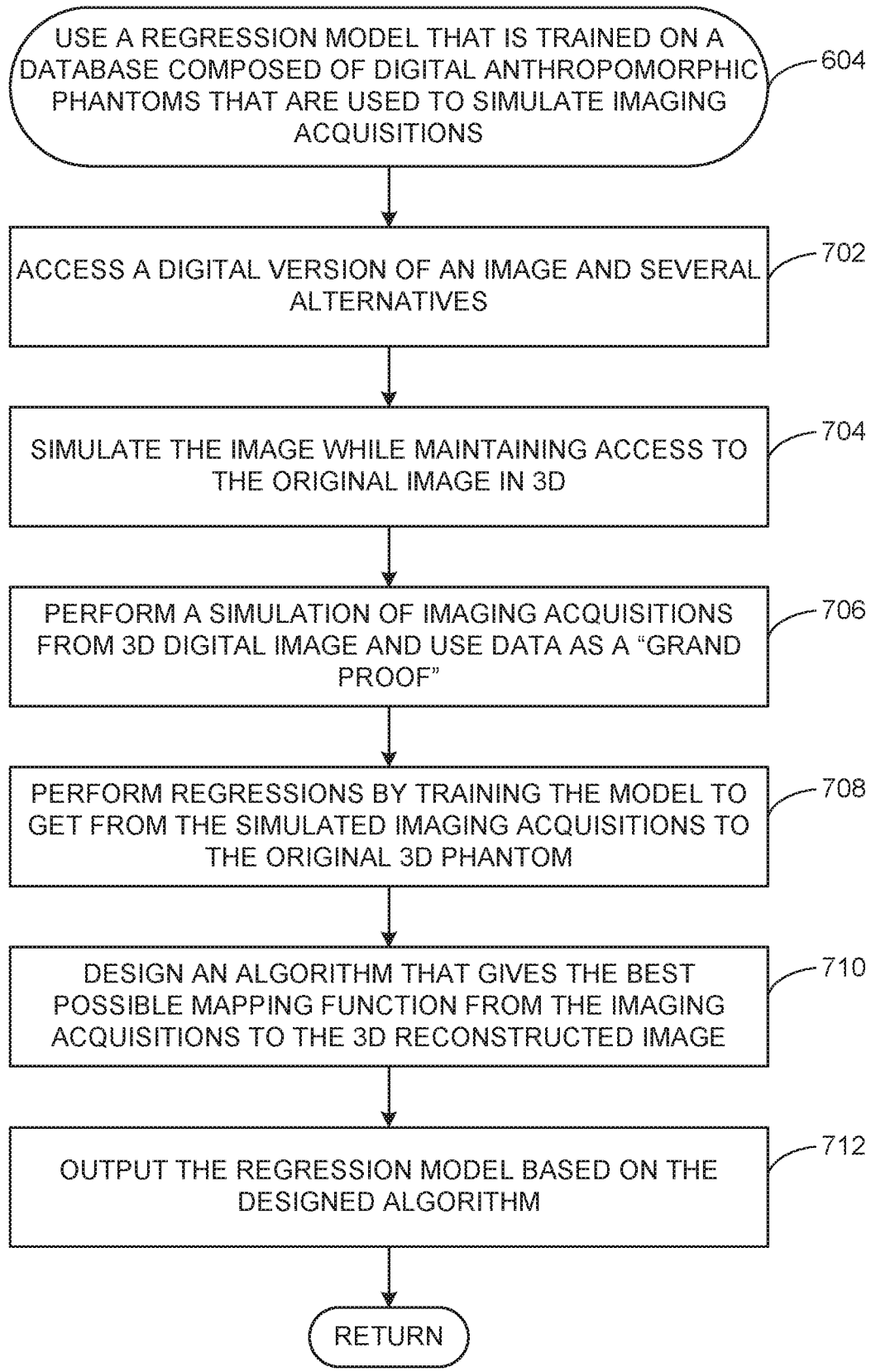
FIG. 7 is a flowchart representative of an example method to use a regression model that is trained on a database composed of digital anthropomorphic phantoms.

FIG. 7 is a flowchart representative of an example implementation of using a regression model that is trained on a database composed of DAPs used to simulate imaging acquisitions (block 604 of FIG. 6). At block 702, the regression model trainer 402 (FIGS. 4A-4E) accesses a digital version of an image and several alternatives. For example, the regression model trainer 402 accesses a digital 3D breast that requires reconstruction. In some examples, the regression model trainer 402 is given the acquisition of the image by the reconstruction controller 301, the voxel reconstructor 434, or the pixel reconstructor 452. However, in other examples, the regression model trainer 402 requests the acquisition of the image from the reconstruction controller 301, the voxel reconstructor 434, or the pixel reconstructor 452. At block 704, the acquisition simulator 410 (FIGS. 4A-4E) within the DAP modeler 404 simulates the image while maintaining access to the original 3D image. In this example, the regression model trainer 402 maintains access to the original 3D image of the breast, and also simulates the image on the DAP acquisition simulator 410. At block 706, the DAP acquisition simulator 410 performs a simulation of imaging acquisitions from the 3D digital image and use the data as "grand proof." In the illustrated example, the simulation of the original 3D image of the breast is used as grand proof. At block 708, the regression model trainer 402 performs regressions by training the model to get from the simulated imaging acquisitions to the original 3D phantom. For example, the regression model trainer 402 performs regressions to get from simulated DBT acquisitions to the original 3D phantom. At block 710, the DAP algorithm creator 414 designs an algorithm that gives the best possible mapping function from the imaging acquisitions to the 3D reconstructed image. In this example, the best possible mapping from the DBT acquisitions to the original 3D phantom is used to design a new algorithm. At block 712, the DAP modeler 404 outputs the regression model based on the designed algorithm. For example, the trained regression model based on the designed algorithm from block 710 is used to reconstruct a voxel 312 or a pixel 314 (FIGS. 3A-3E) in the voxel reconstructor 434 or the pixel reconstructor 452.

Figure 8:
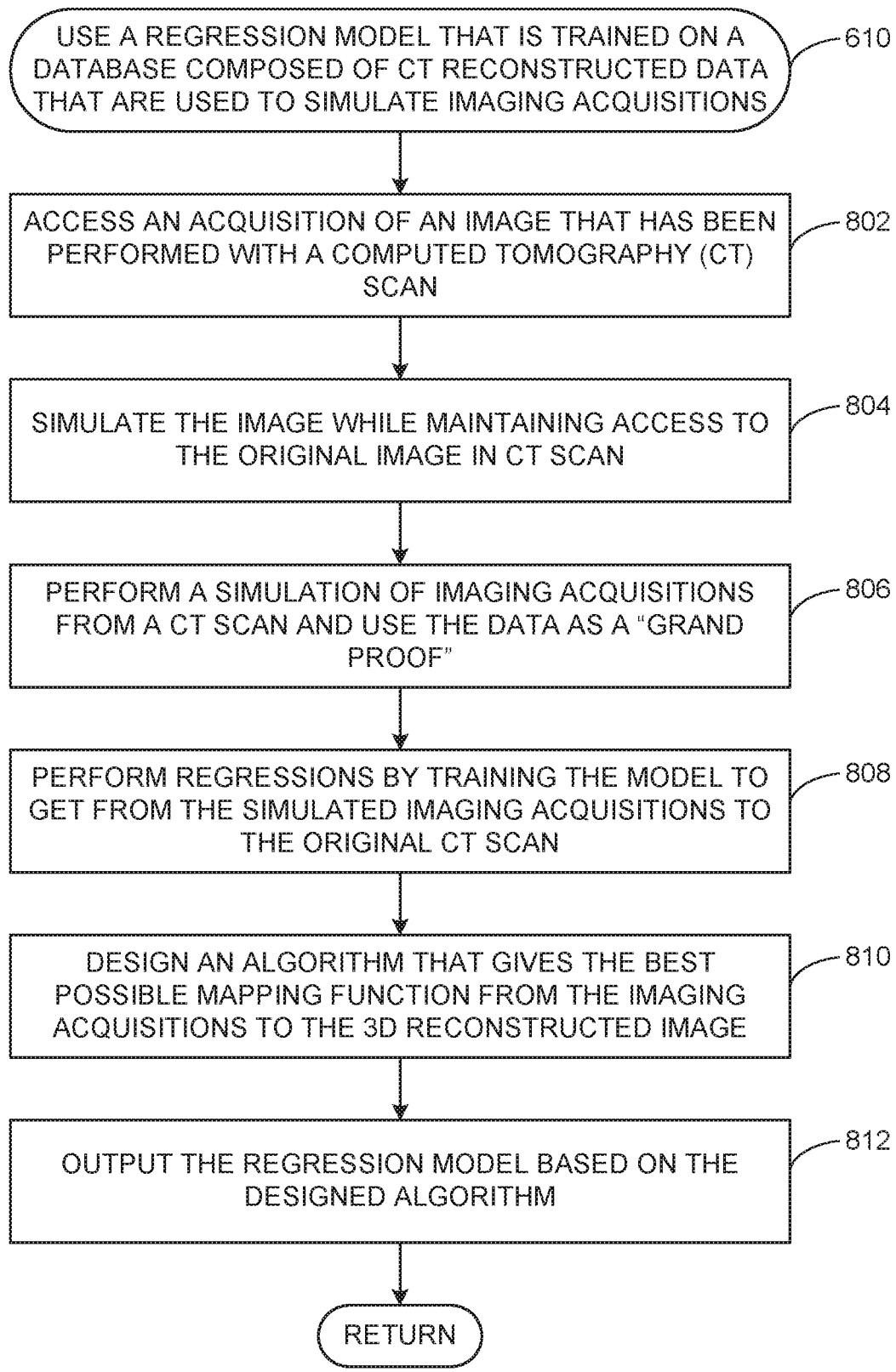
FIG. 8 is a flowchart representative of an example method to use a regression model that is trained on a database composed of computed tomography (CT) reconstructed data.

FIG. 8 is a flowchart representative of an example implementation of using a regression model that is trained on a database of CT reconstructed data to simulate imaging acquisitions (block 610 of FIG. 6). At block 802, the regression model trainer 402 (FIGS. 4A-4E) accesses an acquisition of an image that has been performed with a computed tomography (CT) scan. For example, the regression model trainer 402 accesses a digital 3D breast that requires reconstruction. In some examples, the regression model trainer 402 is given the acquisition of the image by the reconstruction controller 301, the voxel reconstructor 434, or the pixel reconstructor 452. However, in other examples, the regression model trainer 402 requests the acquisition of the image from the reconstruction controller 301, the voxel reconstructor 434, or the pixel reconstructor 452. At block 804, the CT acquisition simulator 416 within the CT modeler 406 simulates the image while maintaining access to the original image in the CT scan. In this example, the regression model trainer 402 maintains access to the original image of the 3D breast, and also simulates the image on the CT acquisition simulator 416. At block 806, the CT acquisition simulator 416 performs a simulation of imaging acquisitions from the CT scan and use the data as "grand proof." In the illustrated example, the simulation of the original 3D breast is used as grand proof. At block 808, the regression model trainer 402 performs regressions by training the model to get from simulated imaging acquisitions to the original CT scan. For example, the regression model trainer 402 performs regressions to get from simulated DBT acquisitions to the original CT scan. At block 810, the CT algorithm creator 420 within the CT modeler 406 designs an algorithm that gives the best possible mapping function from the imaging acquisitions to the 3D reconstructed image. In this example, the best possible mapping from the DBT acquisitions to the original CT scan is used to design a new algorithm. At block 812, the CT modeler 406 outputs the regression model based on the designed algorithm of block 810. For example, the trained regression model based on the algorithm designed at block 810 is used to reconstruct a voxel 312 or a pixel 314 (FIGS. 3A-3E) in the voxel reconstructor 434 or the pixel reconstructor 452.

Figure 9:
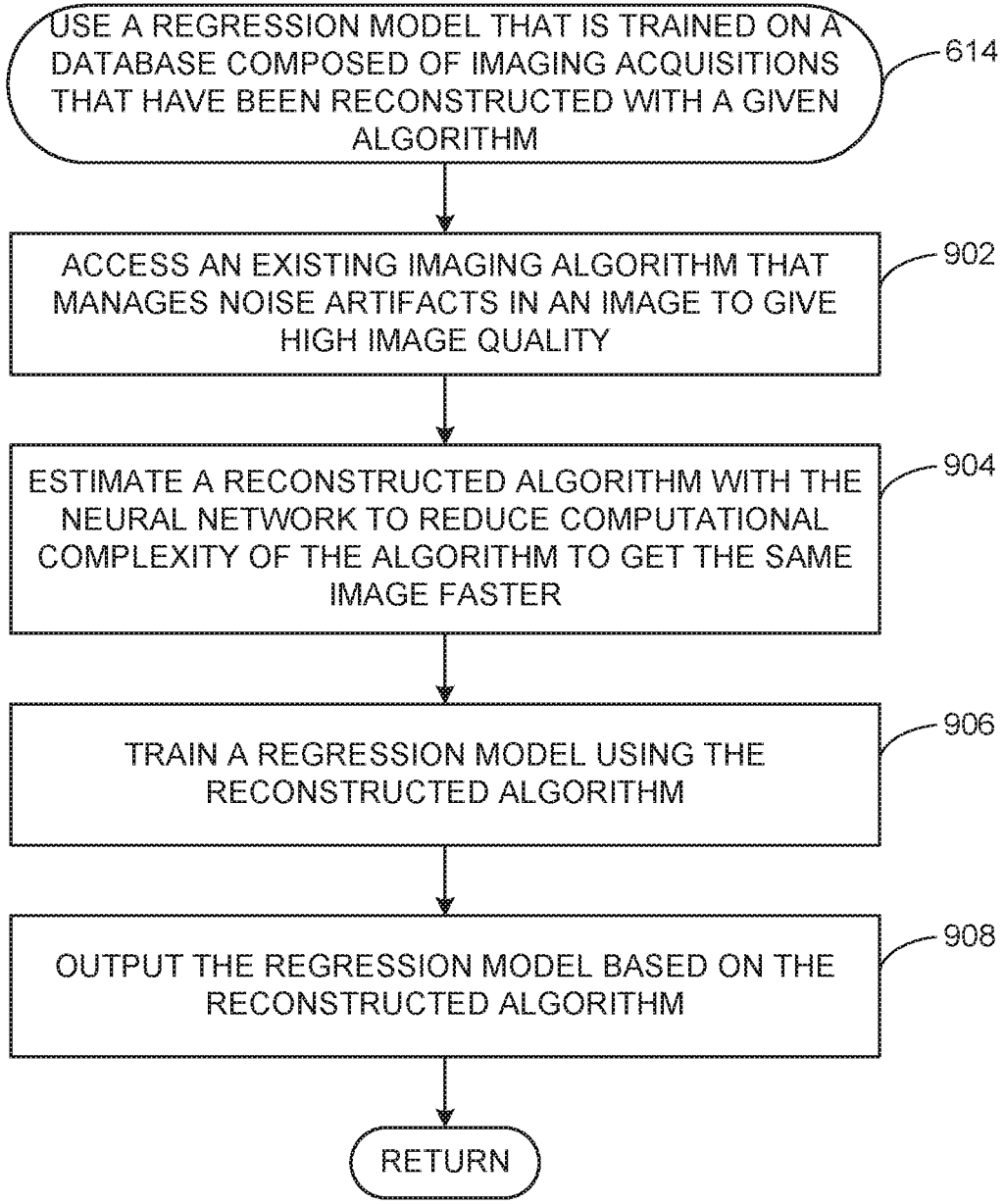
FIG. 9 is a flowchart representative of an example method to use a regression model that is trained on a database composed of imaging acquisitions that have been reconstructed with a given algorithm.

FIG. 9 is a flowchart representative of an example detailed breakdown of block 614 of FIG. 6. At block 614, the reconstruction controller 301 decides to use a regression model that is trained on the algorithm modifier 408. At block 902, the regression model trainer 402 (FIGS. 4A-4E) accesses an existing imaging algorithm from the algorithm database 422 that manages noise artifacts in an image to give high image quality. For example, the regression model trainer 402 accesses a DBT algorithm (e.g., ASiR, MBIR, etc.). At block 904, the acquisition reconstructor 424 within the algorithm modifier 408 estimates a reconstructed algorithm with the neural network to reduce computational complexity of the original algorithm to produce the same image faster. In this example, the neural network reduces the computational power of the DBT algorithm. At block 906, the regression model trainer 402 trains the regression model using the new algorithm to decrease computation time and computation complexity. In the illustrated example, the neural network reduces the computational power of the DBT algorithm. As a result, the same reconstructed image is obtained faster. At block 908, the algorithm modifier 408 outputs the regression model based on the reconstructed algorithm. For example, the trained regression model based on the reconstructed algorithm is used to reconstruct a voxel 312 or a pixel 314 (FIGS. 3A-3E) in the voxel reconstructor 434 or the pixel reconstructor 452.

Figure 10:
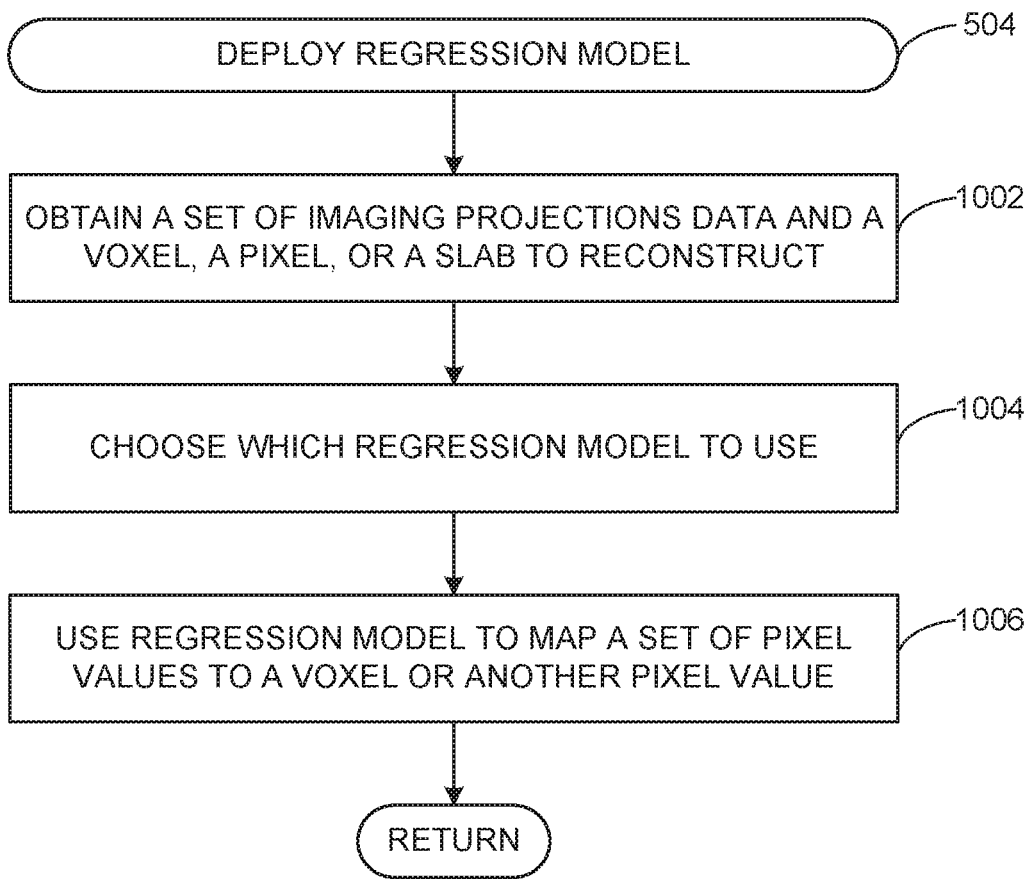
FIG. 10 is a flowchart representative of an example method to deploy a regression model.

FIG. 10 is a flowchart representative of an example implementation of deploying a regression model (block 504 of FIG. 5). At block 1002, the voxel reconstructor 434 or the pixel reconstructor 452 (FIGS. 4A-4E) is given a set of data from the imaging projections data receiver 430, the volume receiver 456, the orientation parameter receiver 460, and/or the thickness parameter receiver 462 and a voxel 312 or a pixel 314 (FIGS. 3A-3E) to reconstruct from the voxel identifier 432 or the pixel identifier 450. For example, the voxel reconstructor 434 may be given a set of DBT projections data from the imaging projections data receiver 430 and a voxel to reconstruct from the voxel identifier 432. At block 1004, the reconstruction controller 301 chooses which regression model to use. In this example, the reconstruction controller 301 decides to use a regression model trained on the DAP modeler 404, the CT modeler 406, and/or the algorithm modifier 408. At block 1006, the voxel projector 436 within the voxel reconstructor 434 or the pixel mapper 454 within the pixel reconstructor 452 uses the regression model to map a set of pixel values to a voxel or another pixel value. The process of mapping a set of pixel values to a voxel or another pixel value was described in detail in FIGS. 1A-2B. In the illustrated example, the regression model trained in the regression model trainer 402 is used to map a set of pixel values to a voxel value. In other examples, a set of pixel values may be mapped to another pixel value to create a synthetic 2D reconstruction.

Figure 11:
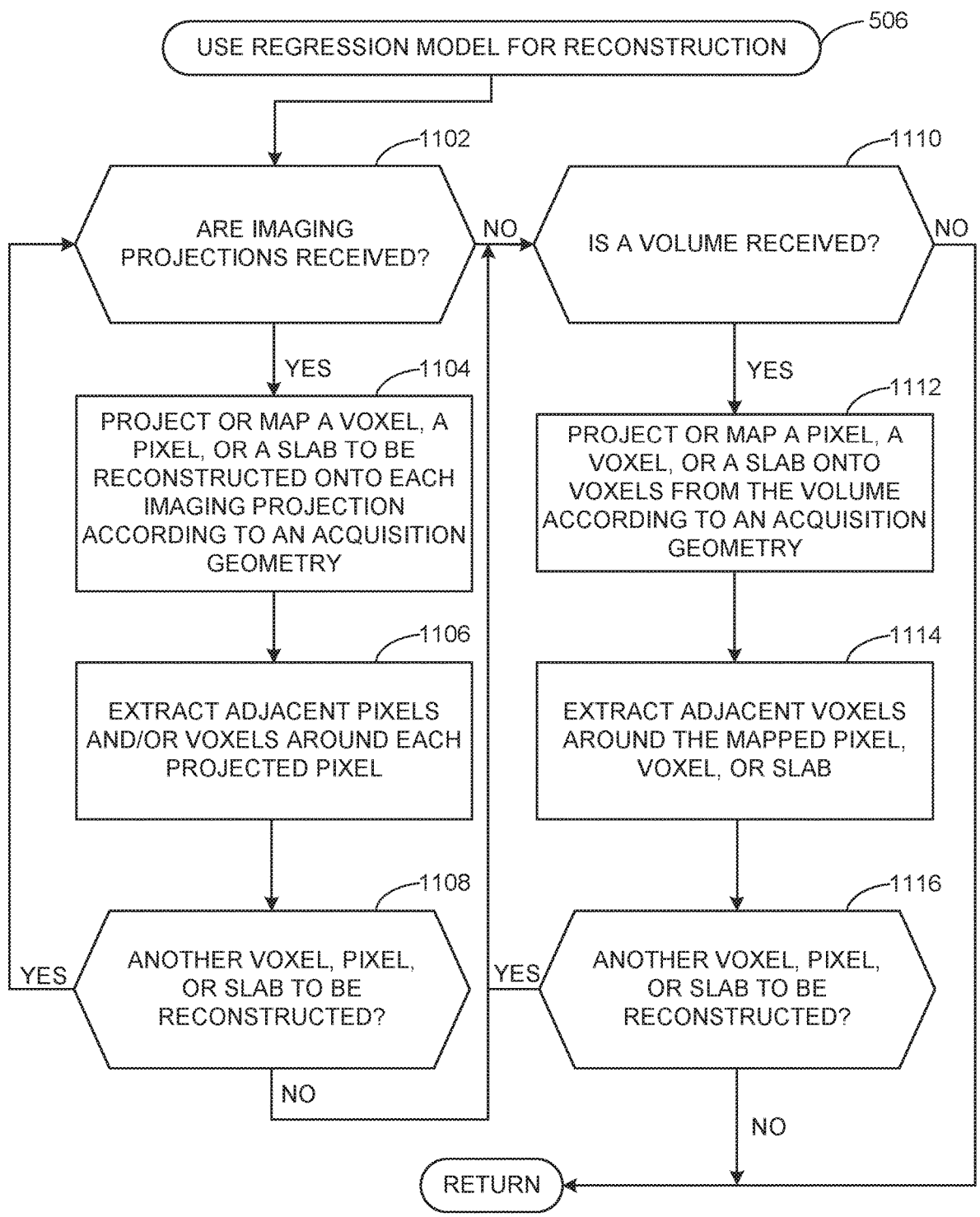
FIG. 11 is a flowchart representative of an example method to use a regression model for reconstruction.

FIG. 11 is a flowchart representative of an example implementation of using a regression model for reconstruction (block 506 of FIG. 5). At block 1102, the reconstructor 306 determines if imaging projections are received. If so, at block 1104, the voxel projector 436, the pixel mapper 454, or the voxel mapper 464 projects or maps a voxel 312 or a pixel 314 (FIGS. 3A-3E) to be reconstructed onto each imaging projection according to an acquisition geometry. For example, a voxel may be projected onto each 2D DBT projection according to the original breast acquisition geometry. This process was previously described in connection with FIGS. 1A-2B. At block 1106, the adjacent pixel extractor 438 and/or the adjacent voxel extractor 458 extracts adjacent pixels and/or adjacent voxels around each projected pixel or voxel. In this example, adjacent pixels around each projected pixel in the voxel are extracted. At block 1108, the reconstructor 306 decides if another voxel 312 or pixel 314 is to be reconstructed. If yes, the process repeats starting at block 1102. In the illustrated example, if there are multiple voxels that require reconstruction, then the process starts over with block 1102. If no, or if imaging projections were not received, the reconstructor 306 determines if a volume is received at block 1110. If yes, at block 1112, the voxel projector 436, the pixel mapper 454, or the voxel mapper 464 projects or maps a voxel 312 or a pixel 314 (FIGS. 3A-3E) to be reconstructed onto each imaging projection according to an acquisition geometry. At block 1114, the adjacent pixel extractor 438 and/or the adjacent voxel extractor 458 extracts adjacent voxels and/or adjacent pixels around the mapped pixel, voxel, or slab. At block 1116, the reconstructor 306 determines if another voxel 312 or pixel 314 is to be reconstructed. If yes, the process repeats starting at block 1110. If no, the process is finished and returns to block 508 of FIG. 5.

Figure 12:
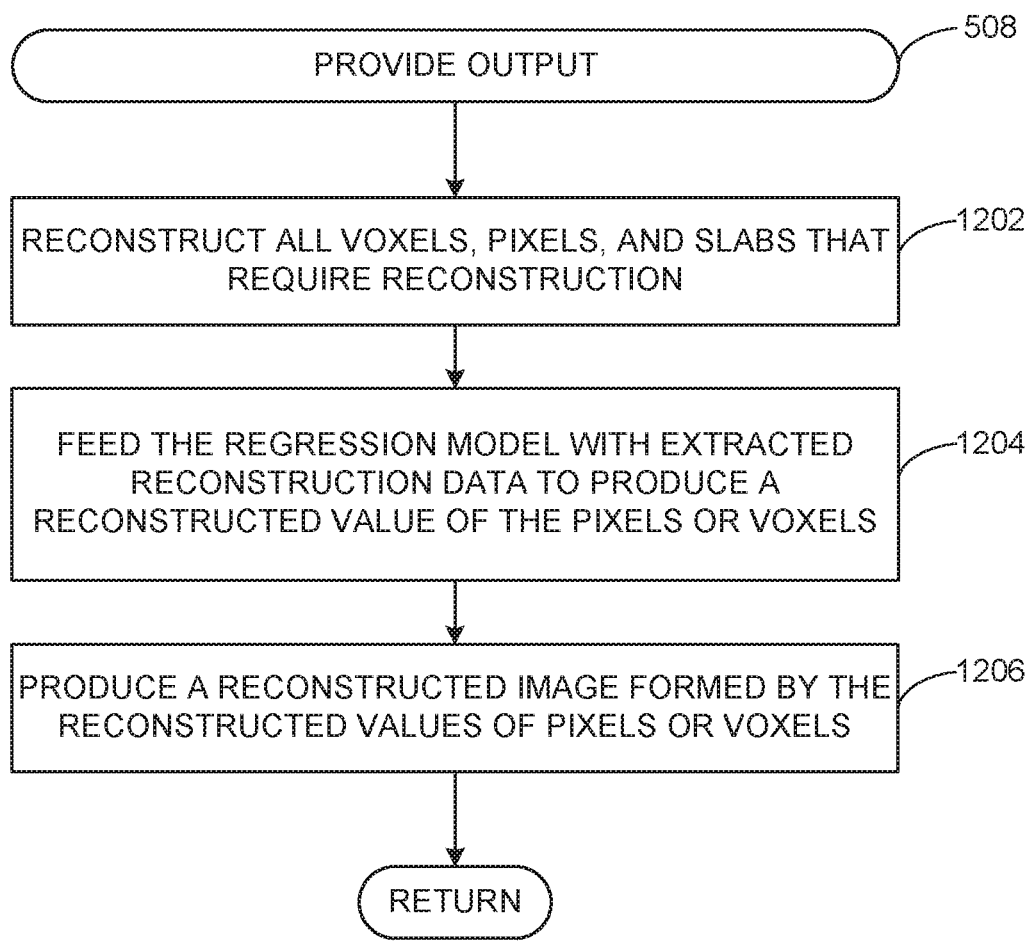
FIG. 12 is a flowchart representative of an example method to provide an output of a reconstructed image.

FIG. 12 is a flowchart representative of an example implementation of providing an output reconstructed image (block 508 of FIG. 5). At block 1202, the voxel reconstructor 434 or the pixel reconstructor 452 reconstructs all voxels 312 and/or pixels 314 (FIGS. 3A-3E) that require reconstruction. For example, if there are 3 voxels in a DBT projections data simulation that require reconstruction, then the voxel reconstructor 434 reconstructs all 3 voxels. At block 1204, the regression model feeder 440 feeds the regression model with extracted reconstruction data to produce a reconstructed value of the pixels and/or voxels at the reconstructed value producer 442. For example, the regression model feeder 440 may feed the regression model with extracted reconstruction data through an artificial neural network (such as a convolutional neural network (CNN), recurrent neural network (RNN), feedforward neural network, etc.), a regression support vector machine (SVM), etc. In the illustrated example, the regression model is fed with extracted voxel reconstruction data to produce a reconstructed value of the voxels in the model of the breast. At block 1206, a reconstructed image is produced formed by example reconstructed image producer 444 using the reconstructed values (e.g., gray values, etc.) of the voxels and/or pixels. In this example, a 3D reconstructed image of the breast is formed by utilizing the reconstructed values of the voxels and/or pixels.

Figure 13:
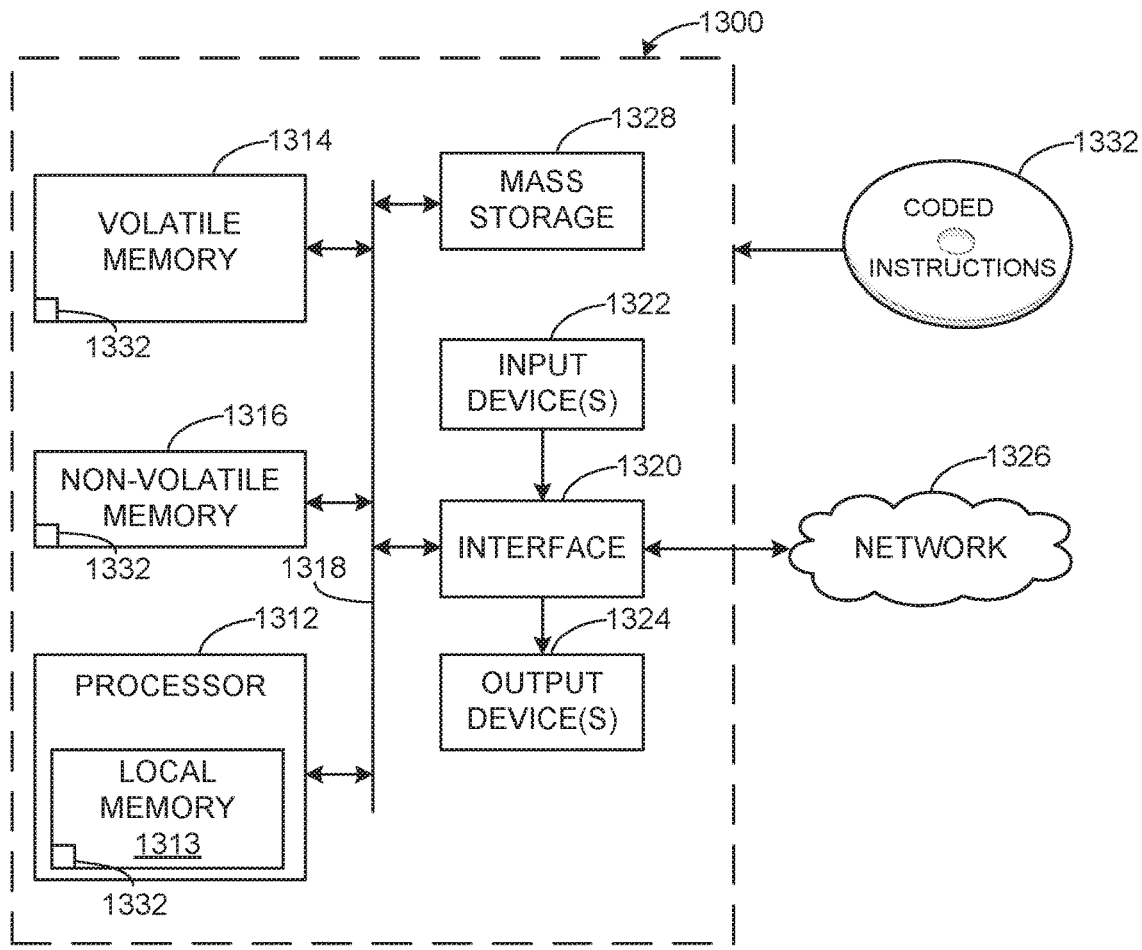
FIG. 13 is a processor diagram which can be used to implement the methods of FIGS. 1-12.

FIG. 13 is a block diagram of an example processor platform 1300 capable of executing the instructions of FIGS. 5-12 to implement the example system 300 of FIGS. 4A-4E. The processor platform 1300 can be, for example, a server, a personal computer, a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, a set top box, or any other type of computing device.

The processor platform 1300 of the illustrated example includes a processor 1312. The processor 1012 of the illustrated example is hardware. For example, the processor 1312 can be implemented by one or more integrated circuits, logic circuits, microprocessors or controllers from any desired family or manufacturer.

The processor 1312 of the illustrated example includes a local memory 1313 (e.g., a cache). The processor 1312 of the illustrated example is in communication with a main memory including a volatile memory 1314 and a non-volatile memory 1316 via a bus 1318. The volatile memory 1314 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1316 may be implemented by flash memory and/or any other desired type of memory device. Access to the main memory 1314, 1316 is controlled by a memory controller.

The processor platform 1300 of the illustrated example also includes an interface circuit 1320. The interface circuit 1320 may be implemented by any type of interface standard, such as an Ethernet interface, a universal serial bus (USB), and/or a PCI express interface.

In the illustrated example, one or more input devices 1322 are connected to the interface circuit 1320. The input device(s) 1322 permit(s) a user to enter data and commands into the processor 1012. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1324 are also connected to the interface circuit 1320 of the illustrated example. The output devices 1024 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 1320 of the illustrated example, thus, typically includes a graphics driver card, a graphics driver chip or a graphics driver processor.

The interface circuit 1320 of the illustrated example also includes a communication device such as a transmitter, a receiver, a transceiver, a modem and/or network interface card to facilitate exchange of data with external machines (e.g., computing devices of any kind) via a network 1326 (e.g., an Ethernet connection, a digital subscriber line (DSL), a telephone line, coaxial cable, a cellular telephone system, etc.).

The processor platform 1300 of the illustrated example also includes one or more mass storage devices 1328 for storing software and/or data. Examples of such mass storage devices 1328 include floppy disk drives, hard drive disks, compact disk drives, Blu-ray disk drives, RAID systems, and digital versatile disk (DVD) drives.

The coded instructions 1332 of FIGS. 4A-4E may be stored in the mass storage device 1328, in the volatile memory 1314, in the non-volatile memory 1316, and/or on a removable tangible computer readable storage medium such as a CD or DVD.

From the foregoing, it will appreciate that the above disclosed methods, apparatus and articles of manufacture facilitate improved image reconstruction and generation of 2D and/or 3D images from projection data, such as DBT projection data. Certain examples facilitate improved modeling of image information to facilitate synthetic 2D image generation from available projection information. Certain examples alleviate dependence on particular equations to instead leverage modeling and learning to generate 2D and/or 3D images from available image projection information. Certain examples facilitate improved application of artificial intelligence techniques to image reconstruction. Certain examples provide technological improvement to processors configured for modeling, processing, and reconstruction of image data, such as 2D and/or 3D images generated from image projection data (e.g., DBT, etc.), etc.

For example, in DBT/CE-DBT, reconstruction directly impacts content of the data for radiologists to review, and, therefore, impacts a resulting diagnosis. While today's algorithms tend to optimize the quality of reconstructed slices (e.g., reducing the noise, mitigating streaking artifacts, etc.), a prior knowledge introduced in these algorithms usually only partially address defects resulting in non-perfect reconstructed data. Additionally, these sophisticated algorithms are usually complex and require significant computational power. Consequently, the design of an ideal reconstruction is limited by the know-how of the algorithm designer. However, for a given voxel, a reconstruction algorithm can simply be seen as a mapping function that associates a reconstructed gray level to a set of input gray levels extracted from the projections.

Thus, certain examples approximate any reconstruction algorithm using regression tools. Certain examples bring a technological improvement to processor reconstruction by learning "ideal" reconstruction that would otherwise be almost impossible to model. Certain examples allow simplifying the design of reconstruction algorithms. For example, computational effort can be lowered by approximating existing algorithms. Additionally, certain examples provide a radiologist with more relevant reconstructed volumes by designing/learning algorithms that would otherwise be difficult to model (e.g., learn ground truth/perfect data, etc.).

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A method comprising:
   receiving a set of digital breast tomosynthesis imaging projections;
   identifying a voxel to reconstruct;
   receiving a trained regression model that maps a set of pixel values to a voxel value, the regression model trained by a regression model trainer based on at least one of acquired projection data or simulated projection data and deployed to map the set of pixel values to the voxel value, wherein the regression model trainer includes at least one of: a) a Digital Anthropomorphic Phantom (DAP) Modeler including an acquisition simulator, an algorithm creator, and a DAP database; b) a Computed Tomography (CT) Modeler including an acquisition simulator, an algorithm creator, and a CT database; or c) an Algorithm Modifier including an acquisition reconstructor and an algorithm database; and
   reconstructing the voxel by:
   projecting the voxel onto each digital breast tomosynthesis imaging projection in the set of digital breast tomosynthesis imaging projections according to an acquisition geometry associated with acquisition of the set of digital breast tomosynthesis imaging projections;
   extracting adjacent pixels around each projected voxel;
   feeding the regression model with data for the extracted adjacent pixels data to produce a reconstructed value for the voxel; and
   repeating the reconstruction for each voxel to be reconstructed to produce a reconstructed image volume.

2. The method of claim 1, further including training the regression model on at least one of:
   a database including acquired projection data and a 2D mammogram acquired under a same compression, the regression model trained to output a 2D image approximately identical to the 2D mammogram when fed with the acquired projection data; or
   a database including simulated projection data and a simulated 2D mammogram acquired under the same compression from a digital anthropomorphic phantom, the regression model trained to output a 2D image approximately identical to the simulated 2D mammogram when fed with the simulated projection data.

3. The method of claim 1, further including training the regression model on at least one of:
   a database including a digital anthropomorphic phantom and simulated projection data obtained from the digital anthropomorphic phantom for a given acquisition geometry, the regression model trained to output a volume approximately identical to the digital anthropomorphic phantom when fed with the simulated projection data;
   a database including computed tomography (CT) reconstructed data and simulated projection data obtained from the CT reconstruction data, the regression model trained to output a volume approximately identical to the CT reconstructed data when fed with the simulated projection data; or
   a database including acquired projection data and reconstructed data from these projection data with a given reconstruction algorithm, the regression model trained to output a volume approximately identical to the reconstructed data when fed with the acquired projection data.

4. The method of claim 1, wherein the voxel is part of a slab to be reconstructed.

5. The method of claim 1, further including producing a reconstructed image using the reconstructed values and displaying the reconstructed image on a user interface.

6. The method of claim 1, further including receiving a volume, the voxel projected onto voxels from the volume according to an acquisition geometry.

7. A system comprising:
a voxel identifier to identify a voxel to be reconstructed;
an imaging projections data receiver to receive a set of digital breast tomosynthesis imaging projections; and
a voxel reconstructor including:
a voxel projector to project the voxel onto each digital breast tomosynthesis imaging projection in the set of digital breast tomosynthesis imaging projections according to an acquisition geometry associated with acquisition of the set of digital breast tomosynthesis imaging projections;
an adjacent pixel extractor to extract adjacent pixels around each projected voxel; and
a regression model feeder to feed a trained regression model with data for the extracted adjacent pixels to produce a reconstructed value of the voxel, the regression model trained by a regression model trainer based on at least one of acquired projection data or simulated projection data and deployed to map a set of pixel values to a voxel value, wherein the regression model trainer includes at least one of: a) a Digital Anthropomorphic Phantom (DAP) Modeler including an acquisition simulator, an algorithm creator, and a DAP database; b) a Computed Tomography (CT) Modeler including an acquisition simulator, an algorithm creator, and a CT database; or c) an Algorithm Modifier including an acquisition reconstructor and an algorithm database, the regression model feeder to repeat the reconstruction for each voxel to be reconstructed to produce a reconstructed image volume.

8. The system of claim 7, wherein the regression model trainer includes:
a database including acquired projection data and a 2D mammogram acquired under the a same compression, the regression model trained to output a 2D image approximately identical to the 2D mammogram when fed with the projection data; or
a database including simulated projection data and a simulated 2D mammogram acquired under the same compression from a digital anthropomorphic phantom, the regression model trained to output a 2D image approximately identical to the simulated 2D mammogram when fed with the simulated projection data.

9. The system of claim 7, further including a feedback generator to identify if a mistake has made on the reconstructed image volume and communicate to the regression model trainer to re-train the regression model.

10. The system of claim 7, wherein the voxel is part of a slab to be reconstructed.

11. The system of claim 7, further including a reconstructed value producer to produce a reconstructed value for each reconstructed pixel or voxel, the reconstructed values used to produce the reconstructed image volume.

12. The system of claim 7, further including a user interface, the user interface to display the reconstructed image volume.

13. A non-transitory computer readable storage medium comprising instructions which, when executed, cause a machine to at least:
receive a set of digital breast tomosynthesis imaging projections;
identify a voxel to reconstruct;
receive a trained regression model that maps a set of pixel values to a voxel value, the regression model trained by a regression model trainer based on at least one of acquired projection data or simulated projection data and deployed to map the set of pixel values to the voxel value, wherein the regression model trainer includes at least one of: a) a Digital Anthropomorphic Phantom (DAP) Modeler including an acquisition simulator, an algorithm creator, and a DAP database; b) a Computed Tomography (CT) Modeler including an acquisition simulator, an algorithm creator, and a CT database; or c) an Algorithm Modifier including an acquisition reconstructor and an algorithm database; and
reconstruct the voxel by:
projecting the voxel onto each digital breast tomosynthesis imaging projection in the set of digital breast tomosynthesis imaging projections according to an acquisition geometry associated with acquisition of the set of digital breast tomosynthesis imaging projections;
extracting adjacent pixels around each projected voxel;
feeding the regression model with data for the extracted adjacent pixels to produce a reconstructed value for the voxel; and
repeating the reconstruction for each voxel to be reconstructed to produce a reconstructed image volume.

14. The non-transitory computer readable storage medium of claim 13, wherein the regression model is trained on at least one of:
a database including acquired projection data and a 2D mammogram acquired under the a same compression, the regression model trained to output a 2D image approximately identical to the 2D mammogram when fed with the projection data; or
a database including simulated projection data and a simulated 2D mammogram acquired under the same compression from a digital anthropomorphic phantom, the regression model trained to output a 2D image approximately identical to the simulated 2D mammogram when fed with the simulated projection data.

15. The non-transitory computer readable storage medium of claim 13, wherein the regression model is trained on at least one of:
a database including a digital anthropomorphic phantom and simulated projection data obtained from the digital anthropomorphic phantom for a given acquisition geometry, the regression model trained to output a volume approximately identical to the digital anthropomorphic phantom when fed with the simulated projection data;
a database including computed tomography (CT) reconstructed data and simulated projections projection data obtained from the CT reconstruction data, the regression model trained to output a volume approximately identical to the CT reconstructed data when fed with the simulated projection data; or
a database including acquired projection data and reconstructed data from these projection data with a given reconstruction algorithm, the regression model trained to output a volume approximately identical to the reconstructed data when fed with the acquired projection data.

16. The non-transitory computer readable storage medium of claim 13, further including instructions which, when executed, cause a machine to identify a mistake within the reconstructed image volume and communicate with the regression model trainer to re-train the regression model.

17. The non-transitory computer readable storage medium of claim 13, wherein the voxel is part of a slab to be reconstructed.

18. The non-transitory computer readable storage medium of claim 13, further including instructions which, when executed cause a machine to produce a reconstructed image onto a user interface using the reconstructed values.

19. The non-transitory computer readable storage medium of claim 13, further including instructions which, when executed cause a machine to receive a volume, the voxels projected onto voxels from the volume according to a geometry acquisition.

* * * * *